US006630163B1

(12) United States Patent
Murad

(10) Patent No.: US 6,630,163 B1
(45) Date of Patent: Oct. 7, 2003

(54) METHOD OF TREATING DERMATOLOGICAL DISORDERS WITH FRUIT EXTRACTS

(76) Inventor: Howard Murad, 4265 Marina City Dr. Penthouse 11, Marina del Rey, CA (US) 90292

( * ) Notice: Subject to any disclaimer, the term of this patent is extended or adjusted under 35 U.S.C. 154(b) by 0 days.

(21) Appl. No.: 09/501,218

(22) Filed: Feb. 10, 2000

Related U.S. Application Data

(60) Provisional application No. 60/130,713, filed on Apr. 22, 1999.

(51) Int. Cl.$^7$ ................................................. A61K 9/20
(52) U.S. Cl. ....................... 424/464; 424/401; 424/725; 424/735; 424/736; 424/744; 424/765; 424/768; 424/59
(58) Field of Search ............................. 424/195.1, 401, 424/59, 278.1, 725, 737, 744, 768, 776, 735, 736, 765, 464; 514/458, 474

(56) References Cited

U.S. PATENT DOCUMENTS

| | | | |
|---|---|---|---|
| 4,857,325 A | 8/1989 | Albeck et al. | 424/195.1 |
| 4,923,697 A | 5/1990 | Albeck et al. | 424/195.1 |
| 5,073,545 A | 12/1991 | Arima et al. | 514/27 |
| 5,124,167 A | 6/1992 | Albeck et al. | 426/542 |
| 5,141,741 A | 8/1992 | Ishida et al. | 424/59 |
| 5,204,105 A | 4/1993 | Mausner | 424/401 |
| 5,290,605 A | 3/1994 | Shapira | 424/439 |
| 5,424,082 A * | 6/1995 | Dake et al. | 426/72 |
| 5,441,740 A | 8/1995 | Ozlen | 424/401 |
| 5,494,667 A | 2/1996 | Uchida et al. | 424/195.1 |
| 5,587,174 A | 12/1996 | Lang et al. | 424/401 |
| 5,747,006 A | 5/1998 | Dornoff et al. | 424/62 |
| 5,747,049 A | 5/1998 | Tominaga | 424/401 |
| 5,776,472 A | 7/1998 | Simon et al. | 424/401 |
| 5,824,320 A | 10/1998 | Rouillard et al. | 424/401 |
| 5,891,440 A | 4/1999 | Lansky | 424/195.1 |
| 5,972,993 A | 10/1999 | Ptchelintsev | 514/449 |
| 5,985,300 A * | 11/1999 | Crotty et al. | 424/402 |
| 6,007,856 A * | 12/1999 | Cox et al. | 426/250 |
| 6,030,622 A * | 2/2000 | Shehadeh | 424/195.1 |

OTHER PUBLICATIONS

Bernadette Eberlein–Konig et al. "Protective effect against sunburn of combined systemic ascorbic acid (vitamin C) and d–α–tocopherol (vitamin E)," *J. Am. Acad. Dermatol.*, v. 38, n. 1, p. 45–48 (Jan. 1998).
"Clarins Chrome", F–D–C Accession No. 02190130012, *The Rose Sheet*, Mar. 30, 1998, vol. 19, Issue 13.
"Pond's Ultra Silk TV Ad Campaign, 'Make Your Face Jealous', to Debut Mar. 2", F–D–C Accession No. 0219008005, *The Rose Sheet*, Feb. 23, 1998, vol. 19, Issue 8.
Chang Teng Fan et al., "Antioxidative Mechanism of Isolated Components from Methanol Extract of Fruit Hulls of *Garcinia mangostana L.*", *Journal of the Chinese Agricultural Chemical Society*, 35(5):540–551 (1997).
"Solgar Gold Specifics Cholesterol Modulators Contains Fermented Red Yeast", F–D–C Accession No. 05050320012, *The Tan Sheet*, Aug. 11, 1997, vol. 5, Issue 32.
"Elizabeth Arden Ceramide Firm Lift, Time Complex to Launch in April", F–D–C Accession No. 02180100000, *The Rose Sheet*, Mar. 10, 1997, vol. 18, Issue 10.
"H$_2$O Plus Suncare Line, Green Tea Unisex Scent Will Bow in First Quarter 1997", F–D–C Accession No. 0217050003, *The Rose Sheet*, Dec. 9, 1996, vol. 17, Issue 50.
"Marketing in Brief: Repechage", F–D–C Accession No. 02170440015, *The Rose Sheet*, Oct. 28, 1996, Vo. 17, Issue 44.
"Del Introducing Naturistics Antioxidant Skin Care Line in February", F–D–C Accession No. 02170440013, *The Rose Sheet*, Oct. 28, 1996, vol. 17, Issue 44.
"H$_2$O Plus Adds Bath Fruits, Exotics Lotions to Body Care Product Mix in Early Fall", F–D–C Accession No. 0217037002, *The Rose Sheet*, Sep. 9, 1996, vol. 17, Issue 37.
"La Prairie Revamped Soleil Suisse Sun Care Line Launching in April", F–D–C Accession No. 02170140007, *The Rose Sheet*, Apr. 1, 1996, vol. 17, Issue 14.
Jonathan Weiss, "Sun Damage & Photoaging," *Skin*, 16–23 (Mar./Apr. 1996).
"Sears Circle of Beauty AHA Serum Offers 12–hour 'Time–Released' Benefit", F–D–C Accession No. 0216038003, *The Rose Sheet*, Sep. 18, 1995, vol. 16, Issue 38.
R.M. Facino, et al., "Echinacoside and caffeoyl conjugates protect collagen from free radical–induced degradation: a potential use of Echinacea Extracts in the prevention of skin photodamage," *Planta Med.*, 61:510–514 (1995).
Karla Werninghaus, et al., "Evaluation of the Photoprotective Effect of Oral Vitamin E Supplementation," *Arch. Dermatol.*, 130:1257–1261 (Oct. 1994).
"Dep Natures Family Shower & Bath Gels Contain Alpha–Hydroxy Acid", F–D–C Accession No. 0215025004, *The Rose Sheet*, Jun. 20, 1994, vol. 15, Issue 25.
"Marketing in Brief: Cosmair," F–D–C Accession No. 02150070012, *The Rose Sheet*, Feb. 14, 1994, vol. 15, Issue 7.

(List continued on next page.)

Primary Examiner—Thurman K. Page
Assistant Examiner—Liliana Di Nola-Baron
(74) Attorney, Agent, or Firm—Pennie & Edmonds LLP

(57) ABSTRACT

This application relates to methods for treating dermatological disorders. The methods include administering a therapeutically effective amount of at least one fruit extract in an amount sufficient to neutralize free radicals; and a pharmaceutically acceptable carrier. Preferred fruit extracts include extracts from apricots, apples, peaches, pears, pineapples, papayas, pomegranates, cherries, kiwis, tangerines and oranges. The most preferred extract is extract from pomegranate.

27 Claims, No Drawings

OTHER PUBLICATIONS

Patricia Mayer, et al., "The Effects of Vitamin E on The Skin," *Cosmetics & Toiletries,* 108:99–109 (Feb. 1993).

Peter T. Pugliese, "A Brief Introduction to Free Radicals and Oxygen Stress," Paper presented at International Conference of Aesthetics and Dermatology, Los Angeles (Feb. 1991).

G. La Rucha et al., "Protective effect of oral selenium plus copper associated with vitamin complex on sunburn cell formation in human skin," *Photodermal Photoimmunol Photomed.,* 8:232–235 (1991).

M. Tierra, *Planetary Herbology,* p. 193–194, (1988).

D.B. Mowrey, *The Scientific Validation of Herbal Medicine,* p. 247–251, 1986.

Dragsted, Lars O. et al., "Cancer–Protective Factors in Fruits and Vegetables: Biochemical and Biological Background," *Pharmaclology & Toxicology,* v. 72, p. S116–135 (1997).

* cited by examiner

METHOD OF TREATING DERMATOLOGICAL DISORDERS WITH FRUIT EXTRACTS

This application claims the benefit of Provisional Application No. 60/130,713, filed Apr. 22, 1999.

TECHNICAL FIELD

The invention relates to dermatological agents containing fruit extracts and methods of using the same to treat dermatological disorders. In particular, the fruit extracts include extracts from apricots, apples, peaches, pears, pineapples, papayas, pomegranates, cherries, kiwis, tangerines, grapes, and oranges.

BACKGROUND OF THE INVENTION

The skin is the most environmentally-stressed organ in mammals, particularly in humans. Not only is the skin subjected to toxic chemicals and hostile environments, but it is also the only organ directly exposed to ultraviolet ("UV") light in the presence of oxygen. [See, e.g., P. Mayer, et al., Cosmetic & Toiletries, 108:99–109 (February 1993)]. Lengthy exposure of the skin to UV light typically damages the skin, resulting in sunburn, photoaging and carcinogenesis.

UV light exposure in the presence of oxygen results in the creation of free radicals. In the skin, these radicals frequently trigger the release of inflammatory mediators, commonly manifested as sun burn; cytoskeletal alterations, breaking down the collagen in the skin; and may also result in structural DNA changes, such as DNA strand breaks and dimer formation. [K. Werninghaus, et al., Arch Dernatol., 130:1257–1261 (October 1994)]. The body attempts to neutralize the free radicals generated by UV light through the use of antioxidants. Antioxidants are commonly found in two forms: enzymatic and non-enzymatic. Superoxide dismutase (SOD), catalase, and glutathione peroxidase are some of the natural enzymatic antioxidants used by the body. SOD accelerates the spontaneous reduction of superoxide free radicals into peroxides and oxygen. Catalase then further decomposes hydrogen peroxide into water and oxygen. Finally, the glutathione peroxidase reduces both hydrogen peroxide and free organic hydroperoxides. Some non-enzymatic antioxidants, such as Vitamin E (tocopherol), Vitamin A (beta-carotene), and Vitamin C (ascorbic acid) have each been individually applied to assist the skin in scavenging free radicals and neutralizing the harmful effects of UV light. [P. Pugliese, "A Brief Introduction to Free Radicals and Oxygen Stress," Paper presented at International Conference of Aesthetics and Dermatology, Los Angeles, (February 1991)]. Conventional skin protection efforts typically attempt to either shield the skin from UV light to prevent the production of free radicals or provide additional agents capable of neutralizing the free radicals.

Topical applications are one such effort known in the art to help shield the skin from the sun's harmful UV effects. These sun-screens often are water- or oil-based lotions or ointments that incorporate photo-protectant materials such as titanium and zinc oxide. [J. Weiss, Skin, 16–23 (March/April 1996)]. Although the most widely used form of protection against exposure to sunlight, these topical applications tend to suffer from several drawbacks. First, large amounts of photo-protective materials are usually incorporated into the topical applications, some of which have recently become suspected of having toxicity or otherwise being harmful under these conditions. Furthermore, the effectiveness of such topical applications is dependent upon a constant and uniform coverage of the skin, which is often difficult to obtain. Many individuals fail to use these topical sunscreens on a regular or continuing basis, as is required under prolonged UV exposure. Finally, sunscreens and other topical applications do not consistently provide good protection for all types of UV light. [Id.].

It is also known that certain fruit extracts may be added to preparations, such as lotions, creams and gels, which are topically applied to the skin, usually for fragrance or conditioning, i.e., softening the skin.

F-D-C Accession No. 02150070012, The Rose Sheet, Feb. 14, 1994, Vol. 15, Issue 7 discloses a skin lotion and cream that combines the benefits of alpha hydroxy acid, antioxidants and sunscreen in one product. The composition is formulated with green tea extract and a triple fruit acid complex to allegedly smooth skin texture, reduce the appearance of fine wrinkles and lines and even out skin tone. The composition also contains a combination of melanin and vitamin E that allegedly neutralizes free radicals before they can damage the skin and an SPF 8 broad spectrum sunscreen.

F-D-C Accession No. 02150250004, The Rose Sheet, Jun. 20, 1994, Vol. 15, Issue 25 discloses a passion flower shower and bath gel that has a fruity fragrance and contains passion flower and extracts of orange flower, mango, strawberry, grapefruit and lavender. Also disclosed is a Vitamin E flower shower and bath gel formula with a light floral fragrance that includes the antioxidant Vitamin E, as well as ginseng, elder flower and rosemary extracts, apricot oil and lavender.

F-D-C Accession No. 02160380003, The Rose Sheet, Sep. 18, 1995, Vol. 16, Issue 38 discloses a triple action complex containing apple extract that allegedly inhibits the effects of irritants and makes skin more resilient, kola nut extract that allegedly defuses the irritation potential of skin-damaging free radicals, bisabool to soothe, and an unspecified antioxidant complex.

F-D-C Accession No. 02170140007, The Rose Sheet, Apr. 1, 1996, Vol. 17, Issue 14 discloses a self tanner formulated with alpha- and beta- hydroxy acids, as well as phytoglycolipids to extend color and prevent skin peeling, an Environmental Protection Complex to neutralize free radicals, and apple extract to help firm skin. The Environmental Protection Complex contains green tea, co-enzyme Q-10 and Vitamins E and C.

F-D-C Accession No. 02170370002, The Rose Sheet, Sep. 19, 1996, Vol. 17, Issue 37 discloses bath and shower gels and body lotions available in pear, pink grapefruit, pomegranate and tangerine fragrances. Also disclosed are body lotions having kiwi fruit, orange peel, apricot, and Vitamin E and provitamins B5 to allegedly help condition skin.

F-D-C Accession No. 02170440013, The Rose Sheet, Oct. 28, 1996, Vol. 17, Issue 44 discloses a pink grapefruit facial soap with grapefruit seed, orange blossom and yarrow extracts that leaves behind a soft, smooth moisturized complexion.

F-D-C Accession No. 02170440015, The Rose Sheet, Oct. 28, 1996, Volume 17, Issue 44 discloses a body wash formulated with seaweed, orange peel extract and sage extract that leaves the skin hydrated and revitalized. Also disclosed is a hand cream containing seaweed, green tea extract, cooling eucalyptus, and shea butter.

F-D-C Accession No. 02170500003, The Rose Sheet, Dec. 9, 1996, Vol. 17, Issue 50 discloses a scent named Green Tea eau de toilette, which has notes of freesia, green pineapple, Granny Smith apple, along with Japanese green tea, pink grapefruit, bergamont, mandarin and mint accords.

F-D-C Accession No. 02180100000, The Rose Sheet, Mar. 10, 1997, Vol. 18, Issue 10 discloses a lotion for face and throat that allegedly provides the immediate perception of firm, uplifted skin using a ceramide retinyl complex, which combines the "anti-aging properties" of ceramide 6 and retinyl linoleate with the tissue respiratory factors found in Vitamin C and apple extract.

F-D-C Accession No. 05050320012, The Tan Sheet, Aug. 11, 1997, Vol. 5, Issue 32 discloses a Fruit Polyphenol Antioxidant Complex "Vegicap" with extracts from cherries, apples, apricots, prunes, pomegranates, quercetin,.and vitamin C. Also disclosed is a formulation including hawthorne berry extract.

F-D-C Accession No. 0219008005, The Rose Sheet, Feb. 23, 1998, Vol. 19, Issue 8 discloses a body lotion moisturizer that combines BHAs, AHAs, vitamins A, E and green tea extract to exfoliate skin while providing antioxidant benefits. Other antioxidants contained in the product include willow, apple and lemon extract blend.

F-D-C Accession No. 02190130012, The Rose Sheet, Mar. 30, 1998, Vol. 19, Issue 13 discloses a Daily Moisture Care cream-gel that pairs Calabria orange extract with antioxidants to allegedly strengthen the skin's natural defense system while keeping skin healthy and supple.

U.S. Pat. No. 4,857,325 to Albeck et al. discloses antioxidant compositions and methods for enhancing the texture of the skin, which compositions are prepared by the water extraction of natural antioxidants from plant substrates. The plant tissues from which these water soluble antioxidants may be obtained are the leaves of spinach, clover, alfalfa, corn, tobacco, onion, garlic and algae. Other suitable plants may also be utilized if the extract of green leaves provides an antioxidant effect. The antioxidant may be used in a variety of cosmetics and is alleged to have a protective effect against ultraviolet light damage to the skin. Therefore, the antioxidant may be applied to the skin to prevent damage caused by radiation from natural sources such as the sun, or from artificial sources, either alone or in combination with other sunscreen agents.

U.S. Pat. No, 4,923,697 to Albeck et al. similarly discloses a water soluble antioxidant obtained from plants of the order Chenopodiales which has the capability of lowering the peroxide level of the skin. The antioxidant is obtained by extraction of the plant tissue with water and thereafter chromatographically separating the antioxidant component.

U.S. Pat. No. 5,124,167 to Albeck et al. similarly discloses such cosmetic compositions including a cosmetically acceptable carrier and an effective amount of a water soluble antioxidants, derived from plant tissues, which is capable of being absorbed into mammalian skin to reduce the peroxide level.

U.S. Pat. No. 5,204,105 to Mausner discloses an emulsified cosmetic composition which reduces puffy skin and dark circles under the eyes, making the contour of the skin smoother, and for reducing sensations of irritation and inflamation of the skin under the eyes. The composition is selected from the group consisting of plant extracts, yeast extracts, and a combination thereof. The plant extracts include butcher broom, hydrocotyl, horse chestnut, calendula, hamamelis, horsetail, euphrasia, peach, lady's mantle, ivy, chamomile matricaria and comfrey.

U.S. Pat. No. 5,441,740 to Ozlen discloses a cosmetic composition containing at least one alpha-hydroxy acid, salicylic acid and at least one digestive enzyme derived from fruit. Preferably the digestive enzyme is a mixture of bromelain and papain. Bromelain is disclosed as being typically obtained from pineapples and papain is disclosed as being typically obtained from dry papaya latex. The compositions are allegedly useful for treating various cosmetic conditions or dermatological disorders, such as lack of adequate skin firmness, wrinkles, and dry skin.

U.S. Pat. No. 5,587,174 to Lang et al. discloses a skin and hair treatment composition that includes apple wax, as well as methods for obtaining such compositions. The apple wax is obtained by extraction of depectinized apple pomace with a variety of solvents and evaporation of the extract. The apple wax is generally disclosed to have a protective effect on the skin. Compositions according to the invention can take the form of a variety of preparations for the care or protection of skin.

U.S. Pat. No. 5,824,320 to Rouillard et al. discloses a cosmetic or pharmaceutical composition containing mangiferine, or derivatives thereof, of natural origin or obtained by chemical, enzymatic or biological synthesis, as well as compositions containing a mangiferine plant extract, in particular an Apholia or Mangifera leaf extract. Mangiferine and its derivatives, in purified form or contained in plant extracts, possess high anti-ultraviolet, anti-collagenase and anti-elastic activity. Thus, they are alleged to be particularly useful in cosmetic or pharmaceutical compositions intended for the protection of the epidermis against ultraviolet rays, for enhancing the structural quality of the skin and for providing help in combating biological and/or actinic skin aging.

U.S. Pat. No. 5,891,440 to Lansky discloses a phytoestrogen supplement prepared from pomegranate seeds and a method of preparing the supplement. The supplement can be administered orally or topically. The oral phytoestrogen supplement includes a pomegranate extract, prepared by contacting pomegranate seeds with an appropriate solvent that is non-toxic for oral use, and an aqueous extract prepared by contacting water with an herbal mixture that includes schizandra berries and Chinese asparagus root. The topical supplement includes pomegranate oil obtained from pressed pomegranate seeds and coconut milk.

U.S. Pat. No. 5,073,545 to Arima et al. discloses a method for lightening and whitening skin that comprises externally applying a composition including one or more ellagic acid compounds.

U.S. Pat. No. 5,141,741 to Ishida et al. discloses an anti-sunburn skin care composition containing a polyvalent metal salt of an ellagic acid compound and a cosmetic carrier, as well as a method of protecting human skin from sunburn by applying the composition to the human skin.

In addition, various conventional supplements have attempted to boost the body's natural antioxidant activity using vitamins, minerals, and herbs. Vitamin C, for example, is believed to reduce sun damage, and vitamin E has been used topically as an anti-inflammatory agent and for UV-ray protection of cells. Also, carotenoids may have usefulness as antioxidants, protecting against both free radicals and singlet oxygen, a highly reactive, diamagnetic excited state of dioxygen. Moreover, it is thought that minerals are typically needed to maintain the effectiveness of the body's enzymatic antioxidants. Both copper and zinc are thought to be necessary in the proper functioning of SOD. [G. La Ruche & J.-P. Cesarini, *Photoderniatol Photoimmunol Photomed.*, 8:232–235 (1991)]. Manganese is believed to be a cofactor in the mitochondrial form of SOD. Also, selenium is thought to be necessary for glutathione peroxidase activity, one of the enzymatic antioxidants found naturally in the body. Unfortunately, few experiments into the skin-protecting effects of these antioxidants have provided scientific or conclusive results.

In particular, a study that orally administered vitamin E supplements to participants and then tested their response to the sun found that Vitamin E did not mitigate the UV damage, despite the fact that the subjects were given thirteen times the recommended daily allowance. [K. Werninghaus, et al., *Arch. Dermatol.*, 130:1257–1261 (October 1994)]. Furthermore, beta-carotene has been reported to have beneficial effects in some studies, but has had no effect in others. Finally, another study noted the photo-protective effect of the oral administration of butylated hydroxy toluene, but little effect was shown using vitamins C or E.

Certain herbs have also been found helpful in protecting the skin from the sun's harmful effects. Herb extracts such as burdock root, echinacea, yellow dock root and grape seeds posses detoxifying properties that have been individually applied to help the body eliminate harmful free radicals. Burdock root contains the active ingredient inulin, and is useful in treating cancerous skin conditions, as well as inflammation. Echinacoside and caffeoyl derivatives present in echinacea act as antioxidants, which protect the skin when applied topically. [R. Facino, et al., *Planta Med.* 61:510–514 (1995)]. Yellow dock root contains the active constituent chrysarobin, which has been used in the treatment of chronic skin diseases, such as eczema, leprosy, psoriasis, and cancer. [M. Tierra, "Planetary Herbology," p. 194 (1988)]. Potent bioflavanoids, known as oligomeric proanthocyanidins (OPC's), are found in grape seeds. These OPC's are thought to be potent antioxidants possessing 20 times the antioxidant power of vitamin C and 50 times the antioxidant power of vitamin E. These herbs have been individually used both topically and orally to protect the skin from various afflictions.

Other studies have attempted to demonstrate the synergistic effect of a mixture of antioxidants. In one study, the subjects were given selenium and copper along with a vitamin supplement of vitamin A and E. [G. La Ruche & J.P. Cesarini, *Photodermatol Photoimmunol Photomed.*, 8:232–235 (1991)]. Although the supplements did protect the skin cells to some extent against ultraviolet-induced cell damage, they did not prevent light-induced erythema, i.e., redness.

Also, U.S. Pat. No. 5,290,605, discloses a soft drink that provides protection against sun damage. This drink contains a mixture of carotenoids, optionally together with vitamin C, vitamin E, or other effective antioxidants. The above antioxidants are limited to an amount which does not exceed ten vitamin ARDA equivalents of provitamin A per liter of drink.

Nutritional supplements such as Source Naturals' PYC-NOGENOL® COMPLEX™ provide a variety of vitamins, minerals and herb extracts to allegedly protect the body against free radicals. In particular, the PYCNOGENOL® COMPLEX™ contains pycnogenol, proanthodyn, quercetin, Ginkgo Biloba extract, Green Tea extract, Bilberry extract, Silymarin, Tumeric extract, Hawthorn Berry extract, Rosemary extract, vitamin C (in the form of zinc and magnesium ascorbates), and magnesium.

Also, an herbal supplement and nutritional suggestions for the maintenance of the skin are disclosed in "The Scientific Validation of Herbal Medicine" by Daniel B. Mowrey, Ph.D. (p.247–251 1986). The herbal supplement consists of extracts of chaparral, dandelion root, burdock root, licorice root, echinacea, yellow dock root, kelp and cayenne. The reference also suggests the use of the following nutritional supplements: vitamin A, vitamin $B_1$, vitamin $B_2$, vitamin $B_6$, a vitamin B complex, vitamin C, vitamin D, vitamin E, niacinamide, pantothenic acid, para-aminobenzoic acid, biotin, choline, inositol, folic acid, zinc, calcium, magnesium, and potassium.

Fruits, vegetables, and commonly used spice and herbs have also been stated to contain cancer protective factors [L. Dragsted, M. Strube, and J.C. Larsen, *Pharmacology and Toxicology*, v. 72, S1, pp. S116–S135 (1993)].

Although the above references disclose various supplements for the skin and studies concerning these supplements, there is no disclosure or suggestion of dermatological agents containing fruit extracts from apricots, apples, peaches, pears, pineapples, papayas, pomegranates, cherries, kiwis, tangerines, grapes, and oranges and methods of employing one or more of such fruit extracts for managing dermatological conditions.

SUMMARY OF THE INVENTION

The invention relates to methods of managing one or more dermatological conditions in a patient having skin which involves administering to a patient a therapeutically effective amount of a dermatological agent including at least one fruit extract from pomegranate in an amount sufficient to neutralize free radicals and a pharmaceutically acceptable carrier. The dermatological agent may be administered orally or topically. When administered orally it is administered in an amount of between about 1 mg to 2,000 mg per day. When administered topically it is administered in an amount of between about 1 mg to 20,000 mg per day. The dermatological agent may be administered with one or more additional pharmaceutical compositions to facilitate managing the dermatological condition.

The additional pharmaceutical composition may be a moisturizing agent provided in an amount sufficient to facilitate hydration of the skin. The moisturizer may be a mono- or poly-hydroxy acid, a hydrophobic agent or a hydrophilic agent. The mono- or poly-hydroxy acid may be glycolic acid, lactic acid, citric acid, tannic acid, salicylic acid, or a mixture thereof. The hydrophobic agent may be ceramide, borage oil, tocopherol linoleate, dimethicone, glycerine, or a mixture thereof. The hydrophilic agent may be hyaluronic acid, sodium peroxylinecarbolic acid, wheat protein, hair keratin amino acids, or a mixture thereof. Other moisturizing agents include primrose oil, GLA 3, flax seed oil, and mixtures thereof.

The additional pharmaceutical composition may be a sunscreen or sunblock component. The sunscreen or sunblock component may be titanium dioxide, zinc oxide, talc, red veterinary petrolatum, a cinnamate, a benzone, a salicylate, a benzoic acid, a benzophenone, or a mixture thereof.

The additional pharmaceutical composition may also be a cysteine component, a magnesium component, a manganese component, or a selenium component. The additional pharmaceutical component can also be at least one of wild yam root, yellow dock, bupleurum, poria cocos, gentian root, myrrh gum, hawthorn berry extract, marshmallow root, rosemary extract, black cohosh, soy, or ginger.

The additional pharmaceutical composition may also be an anti-inflammatory component in an amount sufficient to inhibit or reduce inflammation, an immunity boosting component provided in an amount sufficient to stimulate the patient's immune system response to prevent or facilitate repair of damaged skin, or an antioxidant. The additional anti-inflammatory component may be a vitamin E source, a transition metal component, aloe vera gel, aloe vera, licorice extract, pilewort, Canadian willow root, zinc, arnica, pile wort, allantoin, or a mixture thereof. The immunity boosting component may be echinacea, echinacea extract, golden seal, or a mixture thereof. The antioxidant may be a catechin-based preparation, a vitamin A source, a ginko biloba extract, a silymarin source, a quercetin compound, a vitamin C source, a carotenoid, or a mixture thereof. The one or more additional pharmaceutical compositions may be administered concurrently with the dermatological supplement.

Another embodiment of the invention relates to methods of managing one or more dermatological conditions in a patient which involves administering to the patient a therapeutically effective amount of a dermatological agent including at least one fruit extract in an amount sufficient to neutralize free radicals, a transition metal component in an amount sufficient to inhibit or reduce inflammation, and a pharmaceutically acceptable carrier. The fruit extract can be obtained from apricots, apples, pears, peaches, pineapples, papayas, pomegranates, cherries, kiwis, tangerines, oranges, grapes, or mixtures thereof. The transition metal component can be zinc. The dermatological agent can be administered orally or topically and can be administered with one or more additional pharmaceutical compositions to manage the dermatological condition. The additional pharmaceutical compositions may be a moisturizer, a sunscreen or sunblock, or a mixture thereof. The one or more additional pharmaceutical composition can be administered concurrently with the composition.

DETAILED DESCRIPTION OF THE PREFERRED EMBODIMENTS

A dermatological agent that advantageously manages dermatological conditions has now been discovered. The dermatological agent may be used alone or in conjunction with another composition, such a sunscreen, to manage dermatological conditions. The dermatological agent includes at least one fruit extract, or a pharmaceutically acceptable salt thereof, in an amount sufficient to neutralize free radicals and a pharmaceutically acceptable carrier. The invention also includes methods of administering a therapeutically effective amount of at least one fruit extract, or pharmaceutically acceptable salt thereof, for management of dermatological conditions. The present methods and dermatological agents advantageously manage dermatological conditions, in part by providing antioxidants that are naturally present in the fruit extracts. Without wishing to be bound by theory, it is believed that these antioxidants facilitate neutralization of free radicals in the skin. In a preferred embodiment the dermatological condition is skin damage from exposure to UV light. It is believed that the antioxidants neutralize free radicals in the skin generated in part by exposure to UV light.

The terms "managing" or "management," as used herein, include one or more of the prevention, treatment, or modification of a dermatological condition. Preferably the terms "managing" or "management," as used herein, include one or more of treatment, or modification of a dermatological condition.

The term "dermatological conditions," as used herein, means conditions present anywhere on the skin caused by aging or extrinsic factors such as sunlight, radiations, air pollution, wind, cold, dampness, heat, chemicals, smoke, and smoking. Dermatological conditions include, but are not limited to, dry skin; dandruff; warts; acne; keratosis; psoriasis; eczema; pruritus; age spots; reduced skin moisture; spider veins; senile purpura; lentigines; melasmas; deepening of skin lines; blotches; wrinkles; blemished skin; nodules; atrophy; rosacea; impetigo; precancerous lesions; elastotic changes characterized by leathery, course, rough, dry and yellowish skin; telangiecatic skin; hyperpigmented skin; hyperkeratotic skin; nail infections; inflammatory dermatoses; and damage to hair including, but not limited to, hair breakage, weathering damage, and thinning of hair.

In a preferred embodiment of the pharmaceutical composition, the fruit extract is present in an amount from about 0.01 to 80 weight percent, preferably from about 0.1 to 20 weight percent, and more preferably from about 0.5 to 10 weight percent. Any fruit extract capable of preventing treating or managing skin disorders and/or skin damage is suitable for use in the dermatological agents and methods of the invention. Preferably however, the fruit extract is obtained from apricots, apples, pears, peaches, pineapples, papayas, cherries, kiwis, pomegranates, tangerines, oranges, grapes, or a combination thereof. More preferably, the fruit extract is obtained from pears, peaches, pineapples, papayas, kiwis, tangerines, and oranges. Most preferably, the fruit extract is obtained from pomegranate. Pomegranate extract contains ellagic acid and other polyphenolic compounds. The fruit extract may be obtained from any part of the plant including, for example, the fruit, the skin or rind of the fruit, the seeds, the bark, the leaves, the roots, or the stem.

Any suitable pharmaceutically acceptable carrier may be used with the dermatological agents, as will be readily apparent to one of ordinary skill in the art. Pharmaceutically acceptable carriers include, but are not limited to, hydroxypropyl cellulose, starch (corn, potato, rice, wheat), pregelatinized starch, gelatin, sucrose, acacia, alginic acid, sodium alginate, guar gum, ethyl cellulose, carboxymethylcellulose sodium, carboxymethylcellulose calcium, polyvinylpyrrolidone, methylcellulose, hydroxyproply methylcellulose, microcrystalline cellulose, polyethylene glycol, powdered cellulose, glucose, croscarmellose sodium, crospovidone, polacrilin potassium, sodium starch glycolate, tragacanth, calcium carbonate, dibasic calcium phosphate, tribasic calcium phosphate, kaolin, mannitol, talc, cellulose acetate phthalate, polyethylene phthalate, shellac, titanium dioxide, carnauba wax, microcrystalline wax, calcium stearate, magnesium stearate, castor oil, mineral oil, light mineral oil, glycerin, sorbitol, mannitol, stearic acid, sodium lauryl sulfate, hydrogenated vegetable oil (e.g., peanut, cottonseed, sunflower, sesame, olive, corn, soybean), zinc stearate, ethyl oleate, ethyl laurate, agar, calcium silicate, magnesium silicate, silicon dioxide, colloidal silicon dioxide, calcium chloride, calcium sulfate, silica gel, castor oil, diethyl phthalate, glyercin, mono- and di-acetylated monoglycerides, propylene glycol, triacetin, alamic acid, aluminum monostearate, bentonite, bentonite magma, carbomer 934, carboxymethylcellulose sodium 12, carrageenan, hydroxyethyl cellulose, magnesium aluminum silicate, pectin, polyvinyl alcohol, povidine, sodium alginate, tragacanth, xanthan gum, and silicones. For example, preferred topical formulations of the pharmaceutical composition may include a silicon-containing carrier, preferably a silicone, but in amounts insufficient to cause substantial irritation. Suitable silicones include cyclomethicone or a mixture of cyclopentasiloxane and dimethicone/vinyldimethicone crosspolymer.

The pharmaceutical composition preferably includes one or more moisturizing agents. "Moisturizing agent," as used herein, is used to include any agent that facilitates hydration of the skin by inhibiting or preventing loss of water from the skin, absorbs water from the atmosphere and hydrates the skin, or enhances the skin's own ability to absorb water directly from the atmosphere, or a combination thereof. Moisturizing agents generally minimize or prevent the skin from drying and cracking. Cracked skin is more susceptible to environmental factors that generate free radicals, which is believed to cause further damage to the skin. Thus, moisturizing or facilitating moisturizing skin reduces damage from free radicals and can help manage many dermatological conditions. Suitable moisturizing agents include, but are not limited to, acidic components, hydrophobic agents, and hydrophilic agents, or combinations thereof. Moisturizers, when used, are typically present in an amount from about 0.01 to 20 weight percent, preferably about 0.05 to 10 weight percent, more preferably from about 0.1 to 1 weight percent of the composition.

Moisturizing agents that are acidic components include mono- or poly-hydroxy acids, tannic acid, and mixtures thereof, or a pharmaceutically acceptable salt or ester thereof. One of ordinary skill in the art will be readily able to select and prepare suitable mono- or poly-hydroxy acids for use in the composition of the invention, for example, alkyl hydroxycarboxylic acids, aralkyl and aryl hydroxycarboxylic acids, polyhydroxy-carboxylic acids, and hydroxy-polycarboxylic acids. One of ordinary skill in the art would typically select one or more of the following mono- or poly-hydroxy acids: 2-hydroxyacetic acid (glycolic acid); 2-hydroxypropanoic acid (lactic acid); 2-methyl 2-hydroxypropanoic acid; 2-hydroxybutanoic acid; phenyl 2-hydroxyacetic acid; phenyl 2-methyl 2-hydroxyacetic acid; 3-phenyl 2-hydroxyacetic acid; 2,3-dihydroxypropanoic acid; 2,3,4-trihydroxybutanoic acid; 2,3,4,5,6-pentahydroxyhexanoic acid; 2-hydroxydodecanoic acid; 2,3,4,5-tetrahydroxypentanoic acid; 2,3,4,5,6,7-hexahydroxyheptanoic acid; diphenyl 2-hydroxyacetic acid; 4-hydroxymandelic acid; 4-chloromandelic acid; 3-hydroxybutanoic acid; 4-hydroxybutanoic acid; 2-hydroxyhexanoic acid; 5-hydroxydodecanoic acid; 12-hydroxydodecanoic acid; 10-hydroxydecanoic acid; 16-hydroxyhexadecanoic acid; 2-hydroxy-3-methylbutanoic acid; 2-hydroxy-4-methylpentanoic acid; 3-hydroxy-4-methoxymandelic acid; 4-hydroxy-3-methoxymandelic acid; 2-hydroxy-2-methylbutanoic acid; 3-(2-hydroxyphenyl) lactic acid; 3-(4-hydroxyphenyl) lactic acid; hexahydromandelic acid; 3-hydroxy-3-methylpentanoic acid; 4-hydroxydecanoic acid; 5-hydroxydecanoic acid; aleuritic acid; 2-hydroxypropanedioic acid; 2-hydroxybutanedioic acid; erythraric acid; threaric acid; arabiraric acid; ribaric acid; xylaric acid; lyxaric acid; glucaric acid; galactaric acid; mannaric acid; gularic acid; allaric acid; altraric acid; idaric acid; talaric acid; 2-hydroxy-2-methylbutanedioic acid; citric acid, isocitric acid, agaricic acid, quinic acid, glucoronic acid, glucoronolactone, galactoronic acid, galactoronolactone, uronic acids, uronolactones, ascorbic acid, dihydroascorbic acid, dihydroxytartaric acid, tropic acid, ribonolactone, gluconolactone, galactonolactone, gulonolactone, mannonolactone, citramalic acid; pyruvic acid, hydroxypyruvic acid, hydroxypyruvic acid phosphate and esters thereof; methyl pyruvate, ethyl pyruvate, propyl pyruvate, isopropyl pyruvate; phenyl pyruvic acid and esters thereof; methyl phenyl pyruvate, ethyl phenyl pyruvate, propyl phenyl pyruvate; formyl formic acid and esters thereof; methyl formyl formate, ethyl formyl formate, propyl formyl formate; benzoyl formic acid and esters thereof; methyl benzoyl formate, ethyl benzoyl formate and propyl benzoyl formate; 4-hydroxybenzoyl formic acid and esters thereof; 4-hydroxyphenyl pyruvic acid and esters thereof; and 2-hydroxyphenyl pyruvic acid and esters thereof. The hydroxy acids are preferably selected from one or more alpha-hydroxy acids or beta-hydroxy acids, more preferably from glycolic, lactic, citric, tannic, or salicylic acid, and most preferably from citric and salicylic acids. It should be understood that one or more ;derivatives of the above acidic component, such as esters or lactones thereof, may also be suitably used. One of ordinary skill in the art will also understand that various hydroxy acids, such as those described in U.S. Pat. Nos. 5,547,988 and 5,422,370, are also suitable for use in the dermatological agents and methods of the invention. The acidic component, when present, is typically included in the composition and methods in an amount sufficient to exfoliate, i.e., remove dead or dying skin cells, from at least a portion of the skin. By removing dead or dying skin cells, the skin is better able to absorb moisture from the atmosphere. The acidic component, when used, is typically present in an amount from about 0.1 to 12 weight percent, preferably from about 1 to 11 weight percent, more preferably from about 4 to 10 weight percent of the composition. For example, the acidic component may be present in an amount of about 0.1 to 3 weight percent citric acid in combination with up to about 2 weight percent salicylic acid.

Moisturizing agents that are hydrophobic agents include, but are not limited to, ceramide, borage oil (linoleic acid), tocopherol linoleate, dimethicone, glycerine, and mixtures thereof. Hydrophobic agents, when present, are believed to moisturize the skin by inhibiting or preventing the loss of water from the skin. The hydrophobic agent, when present, is typically present in an amount from about 0.01 to 2 weight percent, preferably from about 0.05 to 1.5 weight percent, and more preferably from about 0.1 to 1 weight percent of the composition.

Moisturizing agents that are hydrophilic agents include, but are not limited to, hyaluronic acid, sodium peroxylinecarbolic acid (sodium PCA), wheat protein (e.g., laurdimonium hydroxypropyl hydrolyzed wheat protein), hair keratin amino acids, and mixtures thereof. Sodium chloride may also be present, particularly when hair keratin amino acids are included as a moisturizer. Hydrophilic agents, when present, are believed to moisturize the skin by absorbing moisture from the atmosphere to hydrate or facilitate hydration of the skin. The hydrophilic agent, when present, is typically present in an amount from about 0.01 to 2 weight percent, preferably from about 0.05 to 1.5 weight percent, and more preferably from about 0.1 to 1 weight percent of the composition.

Other moisturizing agents that hydrate the skin and are useful in the compositions and methods of the present invention include primrose oil; GLA 3 and other fish oils that may include, for example, the omega-3 and omega-6 oils and/or linoleic acid; and flax seed oil. Preferably, these moisturizing agents are administered orally.

In a preferred embodiment, the dermatological agent includes a mono- or poly-hydroxy acid, tannic acid, or a mixture thereof, or a pharmaceutically acceptable salt or ester thereof, to act as an exfoliant to help remove dead or dying skin cells and improve the skin's own ability to absorb moisture directly from the atmosphere, optionally in combination with one or more hydrophilic agents to help absorb moisture from the atmosphere and hydrate the skin or in combination with one or more a hydrophobic agents to inhibit or prevent moisture loss by the skin.

The pharmaceutical composition may further optionally include one or more of a cysteine component, magnesium component, manganese component, carotenoid component, selenium component, and copper component.

The optional cysteine component assists in thickening the dermis, supplementing of collagen and elastic tissue, and consequently, reduction of wrinkles and other skin conditions. The cysteine component, when used in the composition, is preferably N-acetyl cysteine, or a pharmaceutically acceptable salt thereof, and is then typically present in an amount from about 1 to 10 weight percent, preferably from about 2 to 8 weight percent, and more preferably from about 3 to 6 weight percent of the composition.

The optional manganese component is the co-factor used by the SOD found in mitochondria. The manganese component may be any manganese compound, or pharmaceutically acceptable salt thereof, but preferably is manganese ascorbate or a manganese ascorbic acid complex. The manganese, when present, is typically present in an amount from about 0.5 to 10 weight percent, preferably from about 1 to 8 weight percent and most preferably from about 5 to 7 weight percent, wherein the manganese is present in an amount from about 5 to 20 weight percent of a complex such as manganese ascorbate.

The copper component may also be included in the pharmaceutical composition, and may be any copper compound, or a pharmaceutically acceptable salt thereof. The copper component inhibits elastase and assists in treatment of elastic tissue defects. Preferably, the copper compound is copper sebacate. The copper, when included in the composition, is typically present in an amount from about 5 to 20 weight percent of the copper sebacate. The copper component is typically present in an amount from about 0.01 to 5 weight percent, preferably from about 0.02 to 3 weight percent, and more preferably from about 0.03 to 2 weight percent of the composition.

The magnesium component is also optional and may be any magnesium compound, or a pharmaceutically acceptable salt thereof, but preferably is magnesium ascorbate or magnesium ascorbic acid complex, wherein the magnesium is typically present in about 5 to 20 weight percent of the complex. The magnesium component, when included in the composition, is typically present in an amount from about 1 to 10 weight percent, preferably from about 3 to 8 weight percent, and more preferably from about 5 to 7 percent of the composition.

Additionally, a source of selenium may also be optionally added to the pharmaceutical composition. A selenium compound, or a pharmaceutically acceptable salt thereof, may be used. When present, the selenium compound is preferably selenium complexed with an amino acid. More preferably, the selenium compound is L-selenomethionine, wherein the selenium is present in an amount from about 0.1 to 5 weight percent of the complex. The selenium, when included, is typically present in an amount from about 0.01 to 3 weight percent, preferably from about 0.05 to 2 weight percent, and more preferably from about 0.1 to 1 weight percent in the pharmaceutical composition.

Preferably, the pharmaceutical composition also optionally includes at least one herb from the group of yellow dock, bupleurum, poria cocos, gentian root, myrr gum, hawthorn berry extract, rosemary extract, wild yam root, wild yam extract, marshmallow root, black cohosh, soy, or ginger. These pharmaceutical components are particularly useful in managing dermatological conditions resulting from exposure to ultraviolet light. The synergistic effect of these pharmaceutical components boosts the sun protection factor (SPF) of known sunscreens. Preferably, the use of one or more herbs with the composition will provide a boost of at least about 5 percent, preferably at least about 10 percent, to the SPF of a conventional sunscreen.

Yellow Dock, also known as *Rumex crispus*, is often used to treat skin disease, especially those involving some form of inflammation. The active constituents of yellow dock are believed to be rumicin and chrysarobin. Yellow Dock extract, when included, is typically present in the pharmaceutical composition in an amount from about 1 to 30 weight percent, preferably from about 3 to 25 weight percent, and more preferably from about 5 to 20 weight percent.

Bupleurum, also known as *Bupleurum falactum*, is known for its effect on the liver. The active constituents in bupleurum are believed to be furfurol, sterol, and bupleurumol. The bupleurum, when included, is typically present in the present pharmaceutical composition in an amount from about 1 to 20 weight percent weight, preferably about 2 to 15 weight percent, and more preferably from about 3 to 10 weight percent.

The active constituents in poria cocos, also known as *Lycoperdon solidum*, are tetracyclic titerpenic acids, polysaccharides, ergostol, choline, lipase, and protease. This herb is useful for reducing or eliminating excess fluids from the body. When included in the dermatological agents of the invention, it is typically present in an amount from about 1 to 20 weight percent, preferably from about 2 to 15 weight percent, and more preferably from about 3 to 10 weight percent.

The bitter glycosides in gentian root, also known as *Gentian lutea*, account for its use as a digestive bitter and liver disorder treatment. Gentian root is optionally present in the dermatological agents when used. It is typically present in an amount from about 1 to 20 weight percent, preferably from about 2 to 15 weight percent, and more preferably from about 3 to 10 weight percent.

Myrrh, also known as *Commiphora myrrha*, has several oils, resins and gums that increase circulation and heart rate. Myrrh gum is optionally used in the present pharmaceutical composition. When used, the gum is typically present in an amount from about 1 to 20 weight percent, preferably from about 2 to 15 weight percent, and more preferably from about 3 to 10 weight percent.

Hawthorn berry extract, also known as Crataegus supplement, can optionally be added to the pharmaceutical composition, as well. This herb is useful in the treatment of heart disease. Crategolic acid, citric acid, tartaric acid, glavone, glycosides, and vitamin C are the active constituents of hawthorne berries. The hawthorn berry extract, when included, is typically present in an amount from about 0.5 to 8 weight percent, preferably from about 0.6 to 6 weight percent, and more preferably from about 0.7 to 4 weight percent of the composition.

Rosemary contains aromatic oils that my assist with stomach disorders, and salicylic acid. When included in the composition, rosemary is typically present in an amount from about 0.5 to 8 weight percent, preferably from about 0.6 to 6 weight percent, and more preferably from about 0.7 to 4 weight percent of the composition.

Wild yam possesses glycoside saponins and diosgenins, hormonal precursors to cortical steroids that may help to reduce pain. It is believed to assist with problems of the liver and gall bladder, as well. It is optionally present in the pharmaceutical composition and, when used, is typically present in an amount from about 0.5 to 8 weight percent, preferably from about 0.6 to 6 weight percent, and more preferably from about 0.7 to 4 weight percent.

The marshmallow root, also known as *Althea officinalis*, acts as an anti-inflammatory. The mucilage in the herb soothes membranes, thereby reducing inflammation. Marshmallow root is optionally present in the pharmaceutical composition. When included in the composition, it is typically present in an amount from about 0.5 to 8 weight percent, preferably from about 0.6 to 6 weight percent, and more preferably from about 0.7 to 4 weight percent of the composition.

Black cohosh acts as a natural estrogen supplement. Soy and ginger may act as an anti-oxidant and may act as a moisturizer to hydrate or facilitate hydration of the skin. The amount of these herbs, when present in the dermatological agents of the invention, may be readily determined by one of ordinary skill in the art.

The pharmaceutical composition may also preferably include one or more anti-inflammatory components in an amount sufficient to reduce redness and swelling of the skin, an immunity boosting component in an amount sufficient to boost the immune system to facilitate repair of damaged skin, and one or more additional antioxidants in an amount sufficient to neutralize free radicals, or a combination thereof.

Anti-inflammatory components may prevent and reduce inflammation, including the redness and swelling that often accompanies damaged skin. A transition metal component and/or vitamin E may optionally be included to assist in inhibiting or reducing inflammation.

The optional vitamin E component, when used, is preferably a sulfate or succinate vitamin E complex, or a pharmaceutically acceptable salt thereof, and more preferably a D-alpha tocopherol acid succinate. The vitamin E component, when included, is typically present in topical formulations in an amount from about 5 to 40 weight percent, preferably from about 6 to 30 weight percent, and more preferably from about 7 to 20 weight percent of the composition. When formulated in an oral preparation, the vitamin E may be present in an amount from about 1 to 60 weight percent, preferably from about 5 to 50 weight percent.

The transition metal component, preferably a zinc component, when included in the pharmaceutical composition, prevents or mitigates inflammation and assists in binding collagen fibers within the skin. Transition metals such as zinc are essential to SOD, and thus they affect the body in counteracting free radical formation. The transition metal component, when included, may be any pharmaceutically acceptable type and amount of a transition metal compound, or a pharmaceutically acceptable salt thereof. Preferably, the transition metal is complexed with an amino acid, and more preferably with monomethinone. The transition metal component, when used, is typically present in an amount from about 10 to 30 weight percent of the complex. The transition metal component, when included, is typically present in an amount from about 1 to 12 weight percent, preferably from about 1.5 to 8 weight percent, and more preferably from about 2 to 6 weight percent of the pharmaceutical composition. A unit dose of the transition metal component is typically from about 1 mg to 80 mg, preferably from about 2 mg to 15 mg, and more preferably for oral administration from about 5 mg to 10 mg. Although effective in helping to protect skin from damage, increasing the transition metal component concentration too much, particularly of zinc, in an oral formulation of the pharmaceutical composition may lead to stomach discomfort. One of ordinary skill in the art will be able to readily select a suitable dosage amount particularly in view of the guidelines herein.

Other anti-inflammatory agents optionally used include any pharmaceutically acceptable compounds suitable for administration orally or topically, preferably at least one of aloe vera gel, aloe vera, licorice extract, pilewort, Canadian willow root, zinc, pile wort, arnica, or allantoin. A preferred, although optional, anti-inflammatory agent is allantoin. The anti-inflammatory agents, when present, are used in an amount sufficient to inhibit or reduce inflammation, preferably in an amount from about 0.1 to 2 weight percent, preferably from about 0.3 to 1.5 weight percent, and more preferably from about 0.3 to 1 weight percent of the composition. It should be understood, with reference to managing dermatological conditions, that the anti-inflammatory agents facilitate inhibition or suppression of inflammation anywhere on or in the skin or in adjacent bodily tissues.

Additional anti-oxidants of both the enzymatic and non-enzymatic type may be included in the dermatological agents and methods of the invention. For example, superoxide dismutase (SOD), catalase, and glutathione peroxidase are natural enzymatic anti-oxidants used by the body that may be included with the dermatological agents and pharmaceutical compositions herein. Suitable non-enzymatic anti-oxidants include Vitamin E (e.g., tocopherol), Vitamin A (retinol), Vitamin C (ascorbic acid), carotenoids, echinacoside and caffeoyl derivatives, oligomeric proanthocyanidins or proanthanols (e.g., grape seed extract), silymarin (e.g., milk thistle extract, *Silybum marianum*), ginkgo biloba, green tea polyphenols, and the like, and mixtures thereof. Indeed, any pharmaceutically acceptable compounds suitable for administration orally or topically may be used as an anti-oxidant in the dermatological agents of the present invention, either alone or in any combination. Preferably, the anti-oxidant component includes Vitamin E, Vitamin C, or a carotenoid. The anti-oxidant component, when used, is present in an amount sufficient to inhibit or reduce the effects of free-radicals at the skin.

The pharmaceutical composition may include a vitamin C component as an antioxidant, preferably an ascorbic acid, or a pharmaceutically acceptable salt or ester thereof, and more preferably ascorbyl palmitate, dipalmitate L-ascorbate, sodium L-ascorbate-2-sulfate, or an ascorbic salt, such as sodium, potassium, and calcium, or mixtures thereof. When oral formulations of the pharmaceutical composition are used, it is preferred that a non-acidic form of vitamin C be used to reduce the stomach irritation that may occur when using an acidic form. The vitamin C component, when used, is typically present in the pharmaceutical composition in an amount from about 0.1 to 50 weight percent, preferably from about 5 to 40 weight percent, and more preferably from about 10 to 25 weight percent.

An optional vitamin A component may also be included in the composition of the invention, and this preferably is vitamin A palmitate. The vitamin A component, when used, is typically present in an amount from about 5 to 50 weight percent, more preferably from about 6 to 40 weight percent, and most preferably from about 7 to 30 weight percent of the composition. Topical formulations of the composition, however, will typically include the vitamin A component in an amount from about 0.5 to 15 weight percent, preferably from about 1 to 10 weight percent.

Carotenoids are also antioxidants, and they include, for example, beta-carotene, canthaxanthin, zeaxanthin, lycopen, lutein, crocetin, capsanthin, and mixtures thereof. Beta carotene is a carotenoid that is predominantly found in the skin. A carotenoid component, preferably beta carotene, is optionally present in an amount from about 0.1 to 5 weight percent, preferably from about 0.2 to 4 weight percent, and more preferably from about 0.3 to 3 weight percent in the pharmaceutical composition.

The pharmaceutical composition may also include a catechin-based component as an additional antioxidant. These antioxidants are believed to provide roughly 20 times more antioxidative power than vitamin C and 50 times more antioxidative power than vitamin E. The catechin-based preparation is preferably a proanthanol or a proanthocyanidin, and more preferably a proanthanol, which is commonly obtained from grape seed extract. The catechin-based preparation, when used, is typically present in an amount from about 0.1 to 5 weight percent, preferably from about 0.2 to 3 weight percent, and most preferably from about 0.3 to 2 weight percent of the composition.

The composition may also include quercetin powder as an additional antioxidant. Preferably, the quercetin powder is quercetin dihydrate. When included in the composition, the quercetin is typically present in an amount from about 1 to 20 weight percent, preferably from about 2 to 15 weight percent, and more preferably from about 3 to 10 weight percent in the pharmaceutical composition. Other forms of quercetin can be used, if desired.

A silymarin component may also be added to the pharmaceutical composition. The silymarin component provides an antioxidant component that is believed to specifically target the liver. Preferably, milk thistle extract, also known as *Silybum marianum*, can provide the silymarin for inclusion in the present invention. The extract itself typically contains about 70 to 95 weight percent of silymarin. The silymarin component may be present in an amount from about 0.001 to 1 weight percent, preferably from about 0.01 to 0.5 weight percent of the composition.

In another embodiment, Ginkgo Biloba extract is optionally included in the composition. Volatile oils, tannin and resin are believed to be the active constituents of the extract. Ginkgo Biloba supplies antioxidants that are believed to target the brain. Ginkgo Biloba, when used in the composition, is typically present in an amount from about 0.01 to 3 weight percent, preferably from about 0.02 to 2 weight percent, and more preferably from about 0.03 to 1 weight percent in the pharmaceutical composition.

Yet another antioxidant suitable for use in or with the composition includes a polyphenol, preferably a green tea extract. Suitable anti-oxidants will be readily determinable by one of ordinary skill in the art as guided by the disclosure herein.

As noted above, an immunity boosting component may also preferably be included as part of the composition. Immune boosters, such as echinacea and golden seal, facilitate healing of the sun damaged tissues.

Echinacea and its extract are obtained from the Echinacea family of plants, and these components act as immune boosters. Also, they contain several potent antioxidant compounds, such as echinacoside and caffeoyl derivatives. Echinacea, when included, is typically present in an amount from about 1 to 20 weight percent, preferably from about 2 to 15 weight percent, and more preferably from about 3 to 10 weight percent of the composition.

An additional immunity boosting component can be provided by golden seal, also known as *Hydrastis canaderis*. This is optional, but preferably present in the pharmaceutical composition, typically in an amount from about 1 to 20 weight percent, preferably from about 2 to 15 weight percent, and more preferably from about 3 to 10 weight percent of the composition.

The dermatological agent may also be administered concurrently or sequentially with at least one additional dermatological agent, which may include a sunscreen or sunblock, an oral or topical nutritional supplement including at least one antioxidant, or any other topical application. Sunscreens or sunblocks particularly suitable should include at least one of titanium dioxide, zinc oxide, talc, red veterinary petrolatum, a cinnamate, a benzone, a salicylate, a benzoic acid, or a benzophenone. An exemplary cinnamate is octyl methoxycinnamate. An exemplary benzophenone is oxybenzophenone. An exemplary benzoic acid is para-aminobenzoic acid. Exemplary salicylates include homosalicylate or octyl salicylate. An exemplary benzone is oxybenzone. Suitable topical applications, other than sunscreens or topical nutritional supplements, include an antioxidant and at least one of an alpha-hydroxy acid or a beta-hydroxyacid.

The term "pharmaceutically acceptable salt" refers to a salt prepared from pharmaceutically acceptable non-toxic acids or bases including inorganic or organic acids. Examples of such inorganic acids are hydrochloric, hydrobromic, hydroiodic, sulfuric, and phosphoric. Appropriate organic acids may be selected, for example, from aliphatic, aromatic, carboxylic and sulfonic classes of organic acids, examples of which are formic, acetic, propionic, succinic, glycolic, glucuronic, maleic, furoic, glutamic, benzoic, anthranilic, salicylic, phenylacetic, mandelic, embonic (pamoic), methanesulfonic, ethanesulfonic, panthenoic, benzenesulfonic, stearic, sulfanilic, algenic, and galacturonic. Examples of such inorganic bases, for potential salt formation with the sulfate or phosphate compounds of the invention, include metallic salts made from aluminum, calcium, lithium, magnesium, potassium, sodium, and zinc. Appropriate organic bases may be selected, for example from N,N-dibenzylethylenediamine, chloroprocaine, choline, diethanolamine, ethylenediamine, meglumaine (N-methylglucamine), and procaine.

The dermatological agents of the present invention are useful for managing dermatological conditions caused by aging or extrinsic factors including, but not limited to sunlight, radiations, air pollution, wind, cold, dampness, heat, chemicals, smoke, and smoking. The dermatological agents are useful in managing dry skin; dandruff; warts; acne; keratosis; psoriasis; eczema; pruritus; age spots; reduced skin moisture; spider veins; senile purpura; lentigines; melasmas; deepening of skin lines; blotches; wrinkles; blemished skin; nodules; atrophy; rosacea; impetigo; precancerous lesions; elastotic changes characterized by leathery, course, rough, dry and yellowish skin; telangiecatic skin; hyperpigmented skin; hyperkeratotic skin; nail infections; inflammatory dermatoses; damage to hair including, but not limited to, hair breakage, weathering damage, and thinning of hair; and the like. Preferred conditions for treatment include photo-damage, precancerous lesions, wrinkles, and leathery skin. In one embodiment, the dermatological agents are used to prevent, treat, or manage damage caused by exposure to sunlight. The dermatological agents are administered to a patient in need of such treatment or such protection or management in a therapeutically effective amount so as to increase the sun protection factor of the skin.

The phrase "therapeutically effective amount" means the amount of the dermatological agent that provides a therapeutic benefit in the management of a dermatological condition. It should be understood by one of ordinary skill in the art that this amount will vary depending on the condition being treated and the patient and will be readily determinable.

The magnitude of a prophylactic or therapeutic dose of the dermatological agent in the managing a dermatological condition will vary with the sensitivity of the person's skin and the route of administration. The dose, and perhaps the dose frequency, will also vary according to the age, body weight, and response of the individual patient. In general, the total daily dose range, for the conditions described herein, is from about 1 mg to about 2,000 mg administered in about one to ten doses, preferably two to eight doses. The preferred oral daily dose range should be from about 1 mg to 2,000 mg, more preferably from about 400 mg to 1,600 mg, and most preferably from about 800 mg to 1,200 mg. In general, a preferred topical daily dosage range, in single or divided doses, should be from about 1 mg to 20,000 mg, more preferably from about 2,000 mg to 16,000 mg, and most preferably from about 6,000 mg to 10,000 mg of the compositions.

It is further recommended that children, patients aged over 65 years, and those with impaired renal or hepatic function initially receive low doses, and that they then be titrated based on individual response(s) or blood level(s). It may be necessary to use dosages outside these ranges in some cases, as will be apparent to those of ordinary skill in the art. Further, it is noted that the clinician or treating physician will know how and when to interrupt, adjust, or terminate therapy in conjunction with individual patient's response.

Although any suitable route of administration may be employed for providing the patient with an effective dosage of the dermatological agent according to the methods of the present invention, topical and oral administration are preferred. It should be understood that differing routes of administration may be used for the dermatological agent and the additional dermatological agent, sunscreen, sunblock, moisturizing agent, and the like. For example, the dermatological agent can be orally administered while the sunscreen is topically administered. Suitable routes include, for example, oral, rectal, parenteral, intravenous, topical, transdermal, subcutaneous, intramuscular, and similar forms of administration may also be employed. Suitable dosage forms include tablets, troches, dispersions, suspensions, solutions, aerosols, sponges, cotton applicators, capsules, patches, suppositories, and the like.

The dermatological agents used in the methods of the present invention include the active ingredients described above, and may also contain pharmaceutically acceptable carriers, excipients and the like, and optionally, other therapeutic ingredients. The dermatological agents herein may also be administered in conjunction, i.e., concurrently or sequentially, with other skin-protective pharmaceutical compositions or devices, such as a hat, umbrella, or the like.

Dermatological agents for use in the methods of the present invention suitable for oral administration include compositions, such as suspensions, solutions, elixirs, and aerosols; and may include carriers, such as starches, sugars, microcrystalline cellulose, diluents, granulating agents, lubricants, binders, disintegrating agents, and the like. In the case of oral solid preparations (such as powders, capsules, and tablets), the oral solid preparations are typically preferred over the oral liquid preparations.

Dermatological agents for use in the methods of the present invention suitable for topical administration may be presented as discrete units including aerosol sprays, each containing a predetermined amount of the active ingredient, as a powder, stick, or granules, as creams (e.g., a conditioner), pastes, gels, lotions (e.g., a sunscreen), syrups, or ointments, on sponges or cotton applicators, or as a solution or a suspension in an aqueous liquid, a non-aqueous liquid, an oil-in-water emulsion, or a water-in-oil liquid emulsion. Similarly, because of its ease of administration, a cream, lotion, or ointment represents the most advantageous topical dosage unit form.

Dermatological agents for use in the methods of the present invention suitable for oral administration may be presented as discrete units such as capsules, cachets, or tablets, or aerosol sprays, each containing a predetermined amount of the active ingredient, as a powder or granules, as creams, pastes, gels, or ointments, or as a solution or a suspension in an aqueous liquid, a non-aqueous liquid, an oil-in-water emulsion, or a water-in-oil liquid emulsion.

All such dermatological agents may be prepared by any of the methods of a pharmacy, but all methods include the step of bringing into association the carrier(s) with the active ingredient, which constitutes one or more necessary ingredients. In general, the dermatological agents are prepared by uniformly and intimately admixing the active ingredient with liquid carriers or finely divided solid carriers or both, and then, if necessary, shaping the product into the desired presentation.

For example, a tablet may be prepared by compressing or molding, optionally, with one or more accessory ingredients. Compressed tablets may be prepared by compressing in a suitable machine the active ingredient in a free-flowing form such as powder or granules, optionally mixed with a binder, lubricant, inert diluent, surface active or dispersing agent. Molded tablets may be made by molding, in a suitable machine, a mixture of the powdered compound moistened with an inert liquid diluent. Desirably, each tablet, cachet or capsule contains from about 1 mg to 2,000 mg of the active ingredient.

Other suitable dosage forms include tablets, troches, capsules, patches, gel caps, magmas, lozenges, plasters, discs, suppositories, nasal or oral sprays, and the like. When an oral dosage unit form is used instead of a topical dosage form, tablets, capsules, and gel caps are preferred, in which case solid pharmaceutical carriers may be employed. If desired, tablets may be coated by standard aqueous or non-aqueous techniques.

In addition to the common dosage forms set out above, the dermatological agents for use in the methods of the present invention may also be administered by controlled release means and/or delivery devices, such as those described in U.S. Pat. Nos.: 3,845,770; 3,916,899; 3,536,809; 3,598,123; 4,008,719; 5,674,533; 5,059,595; 5,591,767; 5,120,548; 5,073,543; 5,639,476; 5,354,556; and 5,733,566 the disclosures of which are incorporated herein by express reference thereto.

EXAMPLES

The invention is further defined by reference to the following examples describing in detail the preparation of the dermatological agents used in the methods of the present invention. The examples are representative, and they should not be construed to limit the scope of the invention in any way.

Example 1

Apricot/Nectarine Extract Having a Thickened Anhydrous Silicon Base Prepared According to the Invention A dermatological agent according to the invention is prepared as set forth below:

| Ingredient | Trade Name/Supplier | Percent by Weight |
|---|---|---|
| Cyclomethicone | DOW CORNING 245/Dow Corning | 60–80 |
| Silica | AEROSIL/Degussa | 2–15 |
| Tocopheryl Acetate | Vitamin E Acetate/Roche | 0.5–5.0 |
| Apricot (*Prunus Armeniaca*) Extract/Nectarine (*Prunus Persica Nectarina*) Extract | Apricot/Nectarine Polyphenol Extract/ Nutritional Science Int'l | 0.1–20 |

DOW CORNING 245 is commercially available from Dow Corning Corp. of Auburn, MI; AEROSIL is commercially available from Degussa Corporation of Ridgefield Park, NJ; Vitamin E Acetate is commercially available from Roche Holdings Inc. of Wilmington, DE; and Apricot/Nectarine Polyphenol Extract is commercially available from Nutritional Science International Inc. of Massapequa Park, NY.

The ingredients are added in the order given above and are mixed well after each addition. Mixing is continued until the mixture is uniform. The result is a brown, opaque, viscous gel with dark brown specks, having a viscosity of 20,000–40,000 cps. (RVT: #6 at 10 rpm, at 25° C.). The resulting mixture is dispersible in water and ethanol.

Example 2

Apricot/Nectarine Extract in Anhydrous Silicon Base According to the Invention

A dermatological agent according to the invention is prepared as set forth below:

| Ingredient | Trade Name/Supplier | Percent by Weight |
|---|---|---|
| Cyclopentasiloxane (and) Dimethicone/Vinyldimethicone Crosspolymer | SFE839/G.E. Silicones | 80–99.9 |
| Apricot (*Prunus Armeniaca*) Extract/Nectarine (*Prunus Persica Nectarina*) Extract | Apricot/Nectarine Polyphenol Extract/ Nutritional Science Int'l | 0.1–20 |

SFE839 is commercially available from G.E. Silicones of Rochester, NY.

The Apricot/Nectarine Polyphenol Extract is sprinkled into SFE839 while mixing at a moderate speed. Mixing is continued until a uniform mixture is obtained. The result is a brown, opaque, viscous gel with dark brown specks, having a viscosity of 20,000–40,000 cps. (RVT: #6 at 10 rpm, at 25° C.). The resulting mixture is dispersible in water and ethanol.

Example 3

Pomegranate Extract in Anhydrous Silicon Base According to the Invention

A dermatological agent according to the invention is prepared as set forth below:

| Ingredient | Trade Name/Supplier | Percent by Weight |
|---|---|---|
| Cyclopentasiloxane (and) Dimethicone/Vinyldimethicone Crosspolymer | SFE839/G.E. Silicones | 80–99.9 |
| Pomegranate (*Punica Granatum*) Extract | Pomegranate Extract/ Nutritional Science Int'l | 0.1–20 |

The Pomegranate Extract is sprinkled into SFE839 while mixing at a moderate speed. Mixing is continued until a uniform mixture is obtained. The result is a light to dark reddish brown, opaque, viscous gel with dark brown specks, having a viscosity of 20,000–40,000 cps. (RVT: #6 at 10 rpm, at 25° C.). The resulting mixture is dispersible in water and ethanol.

Example 4

Pomegranate Extract in Thickened Anhydrous Silicon Base According to the Invention A dermatological agent according to the invention is prepared as set forth below:

| Ingredient | Trade Name/Supplier | Percent by Weight |
|---|---|---|
| Cyclomethicone | DOW CORNING 245/ Dow Corning | 60–80 |
| Silica | AEROSIL/Degussa | 2–15 |
| Tocopheryl Acetate | Vitamin E Acetate/Roche | 0.5–5.0 |
| Pomegranate (*Punica Granatum*) Extract | Pomegranate Extract/ Nutritional Science Int'l | 0.1–20 |

The ingredients are added in the order given above and mixed well after each addition. Mixing is continued until the mixture is uniform. The result is a light to dark reddish brown, opaque, viscous gel with dark brown specks, having a viscosity of 20,000–40,000 cps. (RVT: #6 at 10 rpm, at 25° C.). The resulting mixture is dispersible in water and ethanol.

Example 5

Combination Skin Treatment

A dermatological agent according to the invention is prepared as set forth below:

| | Ingredient | Trade Name/Supplier | Percent by Weight |
|---|---|---|---|
| Part A | Water (Aqua) | Deionized Water | 17.40–95.38 |
| | Hydroxyethylcellulose | CELLOSIZE POLYMER QP52,000H/Amerchol | 0.1–2.0 |
| Part B | Tetrasodium EDTA | DISSOLVINE 220/Akzo | 0.01–1.0 |
| | Butylene Glycol | 1,3-Butylene Glycol/ Ashland | 0.5–7.0 |
| | Aloe Barbadensis Gel | ALOE CON UP-40/ Florida Food Products | 0.05–5.0 |
| | Methyl Gluceth-10 | GLUCAM E-10/ Amerchol | 0.5–5.0 |
| | Sodium Hyaluronate | HYASOL BT/ Pentapharm | 0.1–5.0 |
| | Zinc Acetate | Zinc Acetate, crystal, U.S.P./N.F./Spectrum | 0.1–2.0 |

-continued

| | Ingredient | Trade Name/Supplier | Percent by Weight |
|---|---|---|---|
| | Dipotassium Glycyrrhizate | Dipotassium Glycyrrhizinate/ International Sourcing | 0.01–0.5 |
| | Lecithin (and) Magnesium Ascorbyl Phosphate (and) (Tocopherol Palmitoyl Hydroxypropyl-trimonium Amylopectin/Glycerin Crosspolymer (and) Lecithin (and) Grape (*Vitis Vinifera*) Seed Extract | OXYSOMES/Barnet | 0.01–3.0 |
| | | GLYCOSPHERE PCO/Kobo | 0.01–3.0 |
| | Lysine Lauroyl Methionate | LIPACIDE LML/Seppic | 0.01–3.0 |
| | Lupin Amino Acids | HYDROLUPIN AA/ Croda | 0.01–3.0 |
| | Chitosan Ascorbate | Ascorbyl Glucosamine/ Collaborative Labs | 0.01–3.0 |
| | Zinc Aspartate | OLIGOIDYNE/ ZINCUM/Vevy | 0.01–3.0 |
| | Pomegranate (*Punica Granatum*) Extract | Pomegranate Extract/ Nutritional Science Int'l | 0.01–3.0 |
| Part C | Alcohol Denat. | SD ALCOHOL 40-B, Anhydrous/Remet | 1.0–15.0 |
| | Salicylic Acid | Salicylic Acid, powder, U.S.P./N.F./Spectrum | 0.5–2.0 |
| Part D | PPG-5-Ceteth-20 | PROCETYL AWS/Croda | 0.5–2.0 |
| | Retinyl Palmitate | Vitamin A Palmitate, type P1.7/Roche | 0.01–0.1 |
| | Linoleic Acid | EMERSOL 315/Henkel | 0.05–2.0 |
| | Orange (*Citrus Aurantium Dulcis*) Oil | Sweet Orange Oil/Berge | 0.01–1.0 |
| | Fragrance (Parfum) | FRAGRANCE - #A11513/779350/ Haarmann & Reimer | 0.01–1.0 |
| Part E | Glycolic Acid | GLYPURE 70% Glycolic Acid/ DuPont | 1.0–10.0 |
| Part F | Sodium Hydroxide | Sodium Hydroxide, pellets, U.S.P./ N.F./Spectrum | 0.1–1.0 |
| | | | 100.00 |

CELLOSIZE POLYMER QP52,000H and GLUCAM E-10 is commercially available from Amerchol Corp. of Edison, NJ; DISSOLVINE 220 is commercially available from Akzo Chemicals Inc. of Deer Park, TX; 1,3 Butylene Glycol is commercially available from Ashland Chemical of Covington, KY; ALOE CON UP-40 is commercially available from Florida Food Products of Eustis, FL; HYASOL is commercially available from Pentapharm AG of Basel, Switzerland; Zinc Acetate, crystal, U.S.P./N.F., Sodium Hydroxide, pellets, U.S.P./N.F., and Salicylic acid, U.S.P./N.F. is commercially available from Spectrum Manufacturing Corp. of New Brunswick, NJ; Dipotassium Glycyrrhizinate is commercial available from International Sourcing Inc. of Upper Saddle River, NJ; OXYSOMES is commercially available from Barnet Products Corporation of Englewood Cliffs, NJ; GLYCOSPHERE PCO is commercially available from Kobo Products Inc. of South Plainfield, NJ; LIPACIDE LML is commercially available from Seppic Inc. of Fairfield, NJ; HYDROLUPINAA and PROCETYL AWS is commercially available from Croda Inc. of Parsippany, NJ; Ascorbyl Glucosamine is commercially available from Collaborative Laboratories of Stony Brook, NY; OLIGOIDYNE ZINCUM is commercially available from Vevy Europe Continental Unit SA of Geneve, Switzerland; SD ALCOHOL 40-B, anhydrous is commercially available from Remet Inc. of Utica, NY; EMERSOL 315 is commercially available from Henkel Corp. of Hoboken, NJ; Sweet Orange Oil is commercially available from Berje of Bloomfield, NJ; FRAGRANCE - #A11513/779350 is commercially available from Haarmann & Reimer Corp. of Teterboro, NJ; GLYPURE 70% Glycolic Acid is commercially available from E.I. DuPont de Nemours and Company of Wilmington, DE.

Deionized water is metered into a processing tank and high speed mixing is started. CELLOSIZE POLYMER QP52,000H is added, the mixture is heated to 75° C., mixed until uniform, and cooled to 40° C. The Part B ingredients are added and mixed until uniform. The premixed ingredients of part C are added and mixed until the mixture is uniform. The premixed ingredients of part D are then added and mixed until a uniform mixture is obtained. The part E ingredients are added and mixing is continued until uniform. The part F ingredients are then added in increments, as needed, to obtain the desired pH. Mixing is continued and the mixture cooled to 35° C. The result is a pale straw, clear to slightly hazy, slightly viscous liquid, having a pH at 25° C. of 3.30–3.80 and a viscosity of 1,600–2,600 cps. (RVT: #3 at 10 rpm and 25° C.).

Example 6

Conditioner for Chemically Treated Hair

A dermatological agent according to the invention is prepared as set forth below:

| | Ingredient | Trade Name/Supplier | Percent By Weight |
|---|---|---|---|
| Part A | Water (Aqua) | Deionized Water | 53.6–97.7 |
| | Guar Hydroxypropyl-trimonium Chloride | JAGUAR C-13S/ Rhodia | 0.05–3.0 |
| | Glycolic Acid | GLYPURE 70% Glycolic Acid/DuPont | 0.01–2.0 |
| | Methylparaben | Methylparaben/ Ashland | 0.05–0.3 |
| | Stearalkonium Chloride | MAQUAT SC-18.85%/Mason | 0.5–5.0 |
| | Cetyl Alcohol | LANETTE 16/Henkel | 0.5–5.0 |
| | Stearyl Alcohol | LANETTE 18/Henkel | 0.5–5.0 |
| | Trimethylsilylamodi-methicone | SF 1708-D1/G.E. Silicones | 0.1–3.0 |
| | Sodium PCA | AJIDEW -50/ Ajinomoto | 0.1–3.0 |
| | Benzophenone-4 | UVINUL MS-40/ BASF | 0.01–0.5 |
| Part B | Hydrolyzed Wheat Protein (and) Hydrolyzed Wheat Starch | CROPEPTIDE W/ Croda | 0.1–3.0 |
| | Hydrolyzed Wheat Protein Silsequioxane | CRODASONE W/ Croda | 0.1–3.0 |
| | Panthenol | Liquid DL-Panthenol 50%/Roche | 0.05–2.0 |
| | Hydrolyzed Soy Protein | HYDROSOY 2000 SF/Croda | 0.05–3.0 |
| | Phytantriol | Phytantriol/Roche | 0.01–1.0 |
| | Polyquatenium-11 | GAFQUAT 755N/ISP | 0.1–3.0 |
| | Methylchloroiso-thiazolinone (and) Methylisothizolinone | KATHON CG/ Rohm & Hass | 0.01–0.1 |
| | Benzalkonium Chloride | BTC-50/Stepan | 0.01–0.5 |
| | FD&C Red No. 40 (CI 16035) | FD&C Red No. 40 (1.0% Solution) | 0.0001–0.001 |
| | Jasmine (*Jasminum* Officinale) Oil (and) Palmarosa (*Cymbopogon Martini*) Oil (and) Sandalwood (*Santalum Album*) Oil (and) Patchouli (*Pogostemon Cablin*) Oil (and) Nutmeg (*Myristica Fragrans*) Oil (and) Grapefruit (*Citrus Grandis*) Oil (and) Orris | ESSENTIAL OIL BLEND "PASSION"/ Prima Fleur | 0.01–1.0 |

-continued

| Ingredient | Trade Name/Supplier | Percent By Weight |
|---|---|---|
| (*Iris Florentina*) Root Oil (and) Carnation (*Dianthus Caryophyllus*) Oil | | |
| Pomegranate (*Punica Granatum*) Extract | Pomegranate Extract/Nutritional Science Int'l | 0.01–3.0 |
| | | 100.00 |

JAGUAR C-13S is commercially available from Rhodia Inc. of Cranbury, NJ; MAQUAT SC-18 85% is commercially available from Mason Chemical Company, Inc. of Joliet, IL; AJIDEW-50 is commercially available from Ajinomoto USA Inc. of Teaneck, NJ; UVINUL MS-40 is commercially available from BASF Corp. of Budd Lake, NJ; GAFQUAT is commercially available from ISP Chemicals Inc. of Calvert City, KY; KATHON CG is commercially available from Rohm & Hass Company, Inc. of North Olmsted, OH; BTC-50 is commercially available from Stepan Company Inc. of Winnetka, IL; ESSENTIAL OIL BLEND "PASSION" is commercially available from Prima Fleur Botanicals Inc. of San Rafael, CA.

Deionized water is metered into a processing tank and high speed mixing is started. JAGUAR C-135 is sprinkled into the water and the mixture is heated to 75° C. The remaining Part A ingredients are added, mixed until uniform, and cooled to 40° C. The Part B ingredients are then added with mixing. Mixing is continued and the mixture is cooled to 35° C. The result is a light peach-colored, opaque, viscous liquid having a pH of 4.00–4.80 at 25° C. and a viscosity of 8,000–12,000 cps. (RVT: #4 at 10 rpm, at 25° C.).

Example 7

Daily Defense Hydrating Sunscreen for Face and Body

A dermatological agent according to the invention is prepared as set forth below:

| | Ingredient | Trade Name/Supplier | Percent By Weight |
|---|---|---|---|
| Part A | Water (Aqua) | Deionized Water | 5.5–91.1 |
| | Carbomer | CARBOPOL ULTREZ 10/B. F. Goodrich | 0.10–1.0 |
| | Methylparaben | Methylparaben/Ashland | 0.1–0.3 |
| | Disodium EDTA | DISSOLVINE Na2X/Akzo | 0.01–0.5 |
| | Sodium PCA | AJIDEW NL-50/Ajinomoto | 0.1–3.0 |
| | Butylene Glycol | 1,3-Butylene Glycol/Ashland | 0.5–6.0 |
| Part B | Stearic Acid | Stearic Acid, triple pressed/Henkel | 0.5–5.0 |
| | Cetyl Alcohol | LANETTE 16/Henkel | 0.5–5.0 |
| | DEA-Cetyl Phosphate | AMPHISOL1/Roche | 0.5–4.0 |
| | Stearyl Dimethicone | DOW CORNING 2503/Dow Corning | 0.1–4.0 |
| | Octyl Methoxycinnamate | PARSOL MCX/Roche | 2.0–7.5 |
| | Benzophenone-3 | UVINUL M-40/BASF | 1.0–6.0 |
| | Butyl Methoxy-dibenzoylmethane | PARSOL 1789/Roche | 2.0–3.0 |
| | Hexyldecyl Benzoate (and) Butyloctyl Benzoate | HALLSTAR AB/CP Hall | 1.0–8.0 |
| | Propylparaben | Propylparaben/Ashland | 0.05–0.2 |
| | Dimethicone | DOW CORNING 200, 350 cs./Dow Corning | 0.1–5.0 |
| | Phenoxyethanol | EMERESSENCE 1160/Henkel | 0.1–1.0 |

-continued

| | Ingredient | Trade Name/Supplier | Percent By Weight |
|---|---|---|---|
| Part C | Triethanolamine | Triethanolamine 99%/Ashland | 0.05–1.0 |
| Part D | Palmitoyl Hydroxypropyltrimonium Amylopectin/Glycerin Crosspolymer (and) Lecithin (and) Grape (*Vitis Vinifera*) Seed Extract | GLYCOSPHERE PCO/Kobo | 0.01–3.0 |
| | Propylene Glycol (and) Water (Aqua) (and) Lemon (*Citrus Medica Limonium*) Peel Extract | ACTIPHYTE OF LEMON BIOFLAVANOIDS PG50/Active Organics | 0.01–3.0 |
| | Lecithin (and) Magnesium Ascorbyl Phosphate (and) Tocopherol | OXYSOMES/Barnet | 0.01–3.0 |
| | Lysine Lauroyl Methionate | LIPACIDE LML/Seppic | 0.01–3.0 |
| | Lupin Amino Acids | HYDROLUPIN AA/Croda | 0.01–3.0 |
| | Chitosan Ascorbate | Ascorbyl Glucosamine/Collaborative Labs | 0.01–3.0 |
| | Zinc Aspartate | OLIGOIDYNE ZINCUM/Vevy | 0.01–3.0 |
| | Pomegranate (*Punica Granatum*) Extract | Pomegranate Extract/Nutritional Science Int'l | 0.01–3.0 |
| | Melanin | SEPIA MELAN INK/Brooks | 0.01–3.0 |
| | Water (Aqua) (and) Glycolipids (and) Hyaluronic Acid | PHYTO/CER HA/Tri-K | 0.01–3.0 |
| | Polyethylene | MICROPOLY 520/Presperse | 0.10–3.0 |
| | Fragrance (Parfum) | FRAGRANCE - #A11515/799628/ Haarman & Reimer | 0.01–1.0 |
| | | | 100.00 |

CARBOPOL ULTREZ 10 is commercially available from B. F. Goodrich Freedom Chemical Company Inc. of Cleveland, OH; HALLSTAR AB is commercially available from CP Hall Co. of Chicago, IL; ACTIPHYTE OF LEMON BIOFLAVANOIDS PG50 is commercially available from Active Organics of Lewisville, TX; PHYTO/CER HA is commercially available from Tri-K Industries Inc. of Northvale, NJ; MICROPOLY 520 is commercially available from Presperse Inc. of Piscataway, NJ.

Deionized water is metered into a processing tank and high speed mixing is started. CARBOPOL ULTREZ 10 is added, the mixture is heated to 80° C., the remaining Part A ingredients added, and mixing continued until a uniform mixture is obtained. In a separate tank the Part B ingredients are heated to 80° C. The Part B ingredients are then added and the mixture is mixed until uniform. The Part C ingredients are added and mixed until uniform. The resulting mixture is cooled to 40° C. and the Part D ingredients are added with mixing. Mixing is continued and the mixture is cooled to 35° C. The result is an off-white, opaque, viscous cream having a pH of 6.00–7.00 at 25° C. and a viscosity of 25,000–35,000 cps. (RVT: #6 at 10 rpm, at 25° C.).

Example 8

Dry Skin Treatment

A dermatological agent according to the invention is prepared as set forth below:

| | Ingredient | Trade Name/Supplier | Percent By Weight |
|---|---|---|---|
| Part A | Water (Aqua) | Deionized Water | 11.5–92.6 |
| | Sclerotium Gum | AMIGEL/Alban-Muller | 0.1–2.0 |
| | Butylene Glycol | 1,3-Butylene Glycol/Ashland | 0.5–6.0 |
| | Methylparaben | Methylparaben/Ashland | 0.05–0.3 |
| | Panthenol | DEXAPANTHENOL/Roche | 0.01–2.0 |
| | Tetrasodium EDTA | DISSOLVINE 220/Akzo | 0.01–5.0 |
| Part B | Isostearic Acid | EMERSOL 875/Henkel | 0.05–5.0 |
| | Cetyl Alcohol | LANETTE 16/Henkel | 0.05–5.0 |
| | DEA-Cetyl Phosphate | AMPHISOLl/Roche | 0.5–4.0 |
| | Glyceryl Stearate (and) PEG-100 Stearate | SIMULSOL 165/Seppic | 0.5–4.0 |
| | Sorbitan Stearate | ARLACEL 60/Uniqema | 0.5–4.0 |
| | Octyl Methoxycinnamate | PARSOL MCX/Roche | 2.0–7.5 |
| | Benzophenone-3 | UVINUL M-40/BASF | 1.0–6.0 |
| | Dimethicone | DOW CORNING 200, 350 cs./Dow Corning | 0.1–3.0 |
| | Caprylic/Capric Triglyceride | LIPONATE GC/Lipo | 0.5–5.0 |
| | Isopropyl Palmitate | LEXOL IPP/Inolex | 0.5–5.0 |
| | Tocopheryl Linoleate | Vitamin E Linoleate/Seltzer | 0.1–2.0 |
| | Cyclomethicone | DOW CORNING 344 Fluid/Dow Corning | 0.1–5.0 |
| Part C | Aloe Barbadensis Gel | ALOE VERA GEL 1X, decolorized /Terry | 0.1–5.0 |
| | Propylene Glycol (and) Water (and) Matricaria (*Chamomilla Recutita*) Extract | ACTIPHYTE OF CHAMOMILE PG50/Active Organics | 0.1–2.0 |
| | Lysine Lauroyl Methionate | LIPACIDE LML/Seppic | 0.01–3.0 |
| | Lupin Amino Acids | HYDROLUPIN AA/Croda | 0.01–3.0 |
| | Chirosan Ascorbate | Ascorbyl Glucoseamine/Collaborative Labs | 0.01–3.0 |
| | Zinc Aspartate | OLIGOIDYNE ZINCUM/Vevy | 0.01–3.0 |
| | Pomegranate (*Punica Granatum*) Extract | Pomegranate Extract/Nutritional Science Int'l | 0.01–3.0 |
| | Sodium Hydroxymethylglycinate | SUTTOCIDE A/Sutton | 0.1–0.6 |
| | Sodium Hyaluronate | HYASOL BT/Pentapharm | 0.1–3.0 |
| | Retinyl Palmitate | Vitamin A Palmitate, type P1.7/Roche | 0.01–0.1 |
| | Dipotassium Glycyrrhizate | Dipotassium Glycyrrhizinate/International Sourcing | 0.1–1.0 |
| | Lecithin (and) Magnesium Ascorbyl Phosphate (and) Tocopherol | OXYSOMES/Barnet | 0.1–3.0 |
| | Palmitoyl Hydroxypropyltrimonium Amylopectin/Glycerin Crosspolymer (and) Lecithin (and) Grape (*Vitis Vinifera*) Seed Extract | GLYCOSPHERE PCO/Kobo | 0.1–3.0 |
| Part D | Glycolic Acid | GLYPURE 70% Glycolic Acid/DuPont | 1.0–10.0 |
| Part E | Sodium Hydroxide | Sodium Hydroxide, pellets, U.S.P./N.F./Spectrum | 0.1–2.0 |
| | | | 100.00 |

AMIGEL is commercially available from Alban-Muller International of Vincennes, France; ARLACEL 60 is commercially available from Indopoco Inc, Iniqema, of Chicago, IL; LIPONATE GC is commercially available from Lipo Chemicals Inc. of Paterson, NJ; LEXOL IPP is commercially available from Inolex Chemical Company Inc. of Philadelphia, PA; Vitamin E Linoleate is commercially available from Seltzer of Carlsbad, CA; ALOE VERA GEL 1X, decolorized is commercially available from Terry Laboratories of Melbourne, FL; SUTTOCIDE A is commercially available from International Specialty Products Inc., ISP Sutton Laboratories of Chatham, NJ.

Deionized water is metered into a processing tank and high speed mixing is started. AMIGEL is sprinkled in and the mixture is heated to 80° C. The remaining Part A ingredients are added and mixed until uniform. In a separate tank the Part B ingredients are heated to 80° C. until dissolved and then added, the mixture is mixed until uniform, and then cooled to 40° C. The Part C ingredients are added and mixed until uniform. The Part D ingredients are added and mixed until uniform. The Part E ingredients are then added in increments, as needed, to obtain the desired pH. Mixing is continued and the mixture cooled to 35° C. The result is a white, opaque, viscous cream having a pH of 3.20–3.70 at 25° C. and a viscosity of 18,000–38,000 cps. (RVT: #6 at 10 rpm, at 25° C.).

Example 9

Eye Complex

A dermatological agent according to the invention is prepared as set forth below:

| | Ingredient | Trade Name/Supplier | % By Weight |
|---|---|---|---|
| Part A | Water (Aqua) | Deionized Water | 6.3–91.7 |
| | PVM/MA Decadiene Crosspolymer | STABILEZE 06/ISP | 0.1–1.0 |
| | Panthenol | Liquid DL-Panthenol 50% /Roche | 0.1–2.0 |
| | Allantoin | Allantoin/ISP | 0.01–1.0 |
| | Methylparaben | Methylparaben/Ashland | 0.05–0.3 |
| | Glycerin | Glycerin 99.5% /Ashland | 0.5–6.0 |
| | Disodium EDTA | DISSOLVINE Na2X/Akzo | 0.01–1.0 |
| Part B | Sodium Hydroxide | Sodium Hydroxide, pellets, U.S.P./N.F./Spectrum | 0.01–2.0 |
| Part C | PPG-12/SMDI Copolymer | POLYOLPREPOLYMER-2/Barnet | 0.5–5.0 |
| | DEA-Cetyl Phosphate | AMPHISOL/Roche | 0.5–3.0 |
| | Cetyl Alcohol | LANETTE 16/Henkel | 0.5–3.0 |
| | Octyl Methoxycinnamate | PARSOL MCX/Roche | 2.0–7.5 |
| | Isopropyl Isostearate | PRISORINE 202/Uniqema | 1.0–6.0 |
| | PEG-100 Stearate (and) Glyceryl Stearate | SIMULSOL 165/Seppic | 0.5–4.0 |
| | Propylparaben | Propylparaben/Ashland | 0.05–0.2 |
| | Tocopheryl Linoleate | Vitamin E Linoleate/Seltzer | 0.05–1.0 |
| | Isostearic Acid | PRISORINE 3505/Uniqema | 0.5–3.0 |
| | Sorbitan Stearate | ARLACEL 60/Uniqema | 0.5–3.0 |

-continued

| | Ingredient | Trade Name/Supplier | % By Weight |
|---|---|---|---|
| | Caprylic/Capric Triglyceride (and) Titanium Dioxide (and) Alumina (and) Polyhydroxystearic Acid (and) Silica | TIOVEIL TG/Tioxide | 0.1–6.0 |
| Part D | Vegetable Oil (and) Beta-Carotene | Beta Carotene in Vegetable Oil 30% / Roche | 0.001–0.1 |
| | Glycolic Acid | GLYPURE 70% Glycolic Acid/ DuPont | 0.5–10.0 |
| | Diazolidinyl Urea | GERMALL II/Sutton | 0.05–0.5 |
| | Retinyl Palmitate | Vitamin A Palmitate, type P1.7/Roche | 0.01–0.1 |
| | Water (Aqua) (and) Glycolipids (and) Hyaluronic Acid | PHYTO/CER HA/Tri-K | 0.05–2.0 |
| | Lecithin (and) Magnesium Ascorbyl Phosphate (and) Tocopherol | OXYSOMES/Barnet | 0.01–3.0 |
| | Dipotassium Glycyrrhizate | Dipotassium Glycyrrhizinate/ International Sourcing | 0.1–1.0 |
| | Palmitoyl Hydroxypropyltrimonium Amylopectin/Glycerin Crosspolymer (and) Lecithin (and) Grape (Vitis Vinifera) Seed Extract | GLYCOSPHERE PCO/Kobo | 0.01–2.0 |
| | Retaglucan | DRAGO-β-GLUCAN/Dragoco | 0.5–5.0 |
| | Lysine Lauroyl Methionate | LIPACIDE LML/Seppic | 0.01–3.0 |
| | Lupin Amino Acids | HYDROLUPIN AA/ Croda | 0.01–3.0 |
| | Chitosan Ascorbate | Ascorbyl Glucoseamine/ Collaborative Labs | 0.01–3.0 |
| | Zinc Aspartate | OLIGOIDYNE ZINCUM/Vevy | 0.01–3.0 |
| | Pomegranate (Punica Granatum) Extract | Pomegranate Extract/Nutritional Science Int'l | 0.01–3.0 |
| | | | 100.00 |

TIOVEIL TG is commercially available from Tioxide Europe S.A. of Palos De La Fontera, Spain; DRAGO-β-GLUCAN is commercially available from Dragoco Inc. of Totowa, NJ.

Deionized water is metered into a processing tank and high speed mixing is started. STABILEZE 06 is sprinkled in, the mixture is heated to 80° C., and mixed for 20 minutes until uniform. The remaining Part A ingredients are added and mixed until uniform. The Part B ingredients are added and mixed until uniform. In a separate tank the Part C ingredients are heated to 80° C. until dissolved, added to the batch, and mixed until uniform. The mixture is then cooled to 40° C. and the Part D ingredients added. Mixing is continued and the mixture is cooled to 35° C. The result is a light yellow, opaque, viscous cream having a pH of 3.80–4.30 at 25° C. and a viscosity of 35,000–47,000 cps. (RVT: #6 at 10 rpm, 25° C.).

Example 10

Night Reform

A dermatological agent according to the invention is prepared as set forth below:

| | Ingredient | Trade Name/Supplier | Percent By Weight |
|---|---|---|---|
| Part A | Water (Aqua) | Deionized Water | 40.2–95.3 |
| | Sclerotium Gum | AMIGEL/Alban-Muller | 0.1–2.0 |
| | Disodium EDTA | DISSOLVINE Na2X/Akzo | 0.05–1.0 |
| | Allantoin | Allantoin/ISP | 0.01–1.0 |
| | Methylparaben | Methylparaben/ Ashland | 0.05–0.3 |
| | Hydrolyzed Oat Flour | RITA VENA 5/ R.I.T.A. | 0.5–4.0 |
| Part B | Dicaprylyl Maleate | BERNEL ESTER DCM/Bernel | 0.5–5.0 |
| | Glyceryl Stearate (and) PEG-100 Stearate | SIMULSOL 165/ Seppic | 0.5–5.0 |
| | PPG-12/SMDI Copolymer | POLYOLPREPOLYMER-2/Barnet | 0.5–5.0 |
| | Pollen Extract (and) Soybean (Glycine Soja) Extract (and) Olive (Olea Europaea) Extract (and) Wheat (Triticum Vulgate) Germ Extract | TRILANOL/Spectrum | 0.5–3.0 |
| | Cetearyl Alcohol (and) Celeareth-20 | HETOXOL D/ Heterene | 0.5–3.0 |
| Part C | Diazolidinyl Urea | GERMALL II/Sutton | 0.05–0.4 |
| | Propylene Glycol (and) Water (Aqua) (and) Raspberry (Rubus Idaeus) Extract | ACTIPHYTE OF RASPBERRY PG50/ Active Organics | 0.01–1.0 |
| | D&C Red No. 33 (Cl 17200) | D&C Red No. 33 (1.0% Solution)/ Hilton-Davis | 0.00001–0.001 |
| | FD&C Yellow No. 5 (Co. 19140) | FD&C Yellow No. 5 (1.0% Solution)/ Hilton-Davis | 0.00001–0.001 |
| | Retinyl Palmitate | Vitamin A Palmitate, type P1.7/Roche | 0.01–0.1 |
| | Dipotassium Glycyrrhizate | Dipotassium Glycyrrhizinate/ International Sourcing | 0.01–1.0 |
| | Lecithin (and) Magnesium Ascorbyl Phosphate (and) Tocopherol | OXYSOMES/Barnet | 0.1–3.0 |
| | Palmitoyl Hydroxypropyltrimonium Amylopectin/ Glycerin Crosspolymer (and) Lecithin (and) Grape (Vitis Vinitera) Seed Extract | GLYCOSPHERE PCO/Kobo | 0.1–3.0 |
| | Water (Aqua) (and) Glycolipds (and) Hyaluronic Acid | PHYTO/CER HA/ Tri-K | 0.01–3.0 |
| | Lysine Lauroyl Methionate | LIPACIDE LML/ Seppic | 0.01–3.0 |
| | Lupin Amino Acids | HYDROLUPIN AA/ Croda | 0.01–3.0 |
| | Chitosan Ascorbate | Ascorbyl Glucosamine/ Collaborative Labs | 0.01–3.0 |
| | Zinc Aspartate | OLIGOIDYNE ZINCUM/Vevy | 0.01–3.0 |
| | Pomegranate (Punica Granatum) Extract | Pomegranate Extract/Nutritional Science Int'l | 0.01–3.0 |
| Part | Salicylic Acid | Salicylic Acid, | 1.0–2.0 |

| Ingredient | Trade Name/Supplier | Percent By Weight |
|---|---|---|
| D Part | | |
| E Sodium Hydroxide | powder, U.S.P./ N.F./Spectrum Sodium Hydroxide, pellets, U.S.P./ N.F./Spectrum | 0.1–2.0 |
| | | 100.00 |

BERNEL ESTER is commercially available from Bernel Chemical Co. of Waldick, NJ; HETOXOL D is commercially available from Heterene Chemical Co. Inc. of Paterson, NJ; RITA VENA is commercially available from R.I.T.A. Corporation of Woodstock, IL.

Deionized water is metered into a processing tank and high speed mixing is started. AMIGEL is sprinkled in and the mixture is heated to 80° C. The remaining Part A ingredients are added and mixed until uniform. In a separate tank the Part B ingredients are heated to 80° C. until dissolved, added to the mixture, mixed until uniform, and cooled to 40° C. The Part C ingredients are added and mixed until uniform. The Part D ingredients are added and mixed until uniform. The Part E ingredients are then added in increments, as needed, to obtain the desired pH. Mixing is continued and the mixture is cooled to 35° C. The result is a very light peach-colored, opaque, viscous liquid having a pH of 3.50–4.00 at 25° C. and a viscosity of 12,000–16,000 cps. (RVT: #5 at 10 rpm, 25° C.).

Example 11

Perfecting Night Cream

A dermatological agent according to the invention is prepared as set forth below:

| | Ingredient | Trade Name/Supplier | Percent By Weight |
|---|---|---|---|
| Part A | Water (Aqua) | Deionized Water | 4.9–93.2 |
| | Carbomer | CARBOPOL 934/ B. F. Goodrich | 0.05–1.0 |
| | Panthenol | DEXAPANTHENOL/ Roche | 0.05–2.0 |
| | Glycerin | Glycerine 99.5% /Ashland | 0.5–6.0 |
| | Methylparaben | Methylparaben/Ashland | 0.05–0.3 |
| Part B | Hybrid Sunflower (Helianthus Annuus) Oil | FLORASUN 90/ Flora Tech | 1.0–6.0 |
| | Squalane | PHYTOLANE/Barnet | 1.0–6.0 |
| | Cetearyl Alcohol (and) Ceteareth-20 | HETOXOL D/Heterene | 0.5–4.0 |
| | Stearic Acid | Stearic Acid, triple pressed/Henkel | 0.5–4.0 |
| | Isostearyl Glycolate | SPECTRON IG76/Spectrum Technologies | 0.5–4.0 |
| | Diacaprylyl Maleate | BERNEL ESTER DCM/Bernel | 1.0–8.0 |
| | Propylparaben | Propylparaben/Ashland | 0.01–0.2 |
| | Evening Primrose (Oenothera Biennis) Oil | EVENING PRIMROSE OIL/Roche | 0.1–2.0 |
| | Borage (Borago Officinalis) Oil | Borage Oil, refined/Barnet | 0.1–2.0 |
| | DEA-Cetyl Phosphate | AMPHISOL/Roche | 0.5–3.0 |
| | Glyceryl Stearate (and) PEG-100 Stearate | SIMULSOL 165/ Seppic | 0.5–4.0 |
| Part C | Triethanolamine | Triethanolamine 99% /Ashland | 0.05–1.0 |
| Part D | Diazolidinyl Urea | GERMALL II/Sutton | 0.5–2.0 |
| | Butylene Glycol (and) (and) Meadowsweet (Spiraea Ulmaria) Extract (and) Honey Extract (Mcl) | ACTIPLEX 1072/ Active Organics | 0.01–2.0 |
| | Water (Aqua) (and) Glycolipids (and) Hyaluronic Acid | PHYTO/CER HA/Tri-K | 0.01–2.0 |
| | Retinyl Palmitate | Vitamin A Palmitate, type P1.7/Roche | 0.05–2.0 |
| | Palmitoyl Hydroxypropyl- trimonium Amylopectin/ Glycerin Crosspolymer (and) Lecithin (and) Grape (Vitis Vinifera) Seed Extract | GLYCOSPHERE PCO/Kobo | 0.01–3.0 |
| | Palmitoyl Hydroxypropyl- trimonium Amylopectin/ Glycerin Crosspolymer (and) Lecithin (and) Camellia Sinensis Extract | GLYCOSPHERE CT/Kobo | 0.01–3.0 |
| | Algae Extract | HAWAIIAN SEAPLANT EXTRACT-J/Tri-K | 0.1–3.0 |
| | Lecithin (and) Magnesium Ascorbyl Phosphate (and) Tocopherol | OXYSOMES/Barnet | 0.01–3.0 |
| | Orange (Citrus Aurantium Dulcis) Oil | SWEET ORANGE OIL/Berje | 0.01–1.0 |
| | Hydrolyzed Soy Flour | RAFFERMINE/R.I.T.A | 0.05–2.0 |
| | Oat (Avena Sativa) Protein | REDUCTINE/R.I.T.A. | 0.05–2.0 |
| | Lysine Lauroyl Methionate | LIPACIDE LML/ Seppic | 0.01–3.0 |
| | Lupin Amino Acids | HYDROLUPIN AA/Croda | 0.01–3.0 |
| | Chitosan Ascorbate | Ascorbyl Glucoseamine/ Collaborative Labs | 0.01–3.0 |
| | Zinc Aspartate | OLIGOIDYNE ZINCUM//Vevy | 0.01–3.0 |
| | Pomegranate (Punica Granatuin) Extract | Pomegranate Extract/Nutritional Science Int'l | 0.01–3.0 |
| | Grapefruit (Citrus Grandis) Oil (and) Orange (Citrus Aurantium Dulcis) Oil (and) Rosewood (Aniba Rosaeodora) Oil (and) Geranium Macula- tum Oil (and) Lavender (Lavandula Angustifolia) Oil (and) Thyme (Thymus Vulgaris) Oil | FRAGRANCE - #A11515/779628/ Haarmann & Reimer | 0.01–1.0 |
| | | | 100.00 |

FLORASUN 90 is commercially available from Flora Tech Inc. of New York, NY.

Deionized water is metered into a processing tank and high speed mixing is started. CARBOPOL 934 is sprinkled in, mixed until dispersed, the solution heated to 80° C., the remaining Part A ingredients added, and mixed until a uniform mixture is obtained. In a separate tank the Part B ingredients are heated to 80° C. until dissolved, added to the mixture, and mixed until uniform. The Part C ingredients are added and mixed until uniform. The mixture is cooled to 40° C. and the Part D ingredients are added. Mixing is continued and the mixture is cooled to 35° C. The result is a white, opaque, viscous liquid having a pH of 6.00–7.00 at 25° C. and a viscosity of 30,000–40,000 cps. (RVT: #6 at 10 rpm, 25° C.).

Example 12

Scalp Treatment for Thinning Hair

A dermatological agent according to the invention is prepared as set forth below:

| | Ingredient | Trade Name/Supplier | Percent By Weight |
|---|---|---|---|
| Part A | Water (Aqua) | Deionized Water | 67.3–99.0 |
| Part B | Propylene Glycol | Propylene Glycol/Ashland | 0.5–5.0 |
| | Methylparaben | Methylparaben/Ashland | 0.5–0.3 |
| Part C | Menthol | Menthol Crystals, U.S.P/Barnet. | 0.01–1.0 |
| | Ethyl Nicotinate | Ethyl Nicotinate/Sigma | 0.01–1.0 |
| | Cinnamon (*Cinnamomum Cassia*) Oil (and) Grapefruit (*Citrus Grandis*) Oil (and) Orange (*Citrus Aurantium Dulcis*) Oil (and) Bitter Orange (*Citrus Aurantium Amara*) Oil | ESSENTIAL OIL BLEND #EE-50098/Ungerer | 0.01–1.0 |
| | Polysorbate 80 | TWEEN 80/Uniqema | 0.1–3.0 |
| | Phytantriol | Phytantriol/Roche | 0.01–1.0 |
| | Biotin | Biotin/Roche | 0.001–0.5 |
| | Salicylic Acid | Salicylic Acid, powder, U.S.P./N.F./Spectrum | 0.01–0.5 |
| | Safflower (*Carthamus Tinctorius* Oil) (and) Capsicum Frutescens Extract | ACTIPHYTE OF CAPSICUM LIPO S CONC./Active Organics | 0.01–0.5 |
| Part D | Diazolidinyl Urea | GERMALL II/Sutton | 0.05–0.4 |
| | Allantoin | Allantoin/ISP | 0.01–1.0 |
| | Tetrasodium EDTA | DISSOLVINE 220/Akzo | 0.01–1.0 |
| | Lactamide MEA | PARAPEL LAM-100/Bernel | 0.05–3.0 |
| | Panthenyl Ethyl Ether | Ethyl Panthenol/Roche | 0.01–2.0 |
| | Cocamidopropyl PG-Dimonium Chloride Phosphate | PHOSPHOLIPID PTC/Uniqema | 0.05–2.0 |
| | Propylene Glycol (and) Saw Palmetto (*Serenoa Serrulata*) Extract | SAW PALMETTO EXTRACT/Chart | 0.01–0.5 |
| | Cyanocobalamin | Vitamin B12/Roche | 0.0001–0.01 |
| | Yeast Extract (Faex) | NAYAD S/Immudyne | 0.05–3.0 |
| | Yeast Extract (Faex) | RESPIROGEN/Immudyne | 0.05–3.0 |
| | Pomegranate (*Punica Granatum*) Extract | Pomegranate Extract/Nutritional Science Int'l | 0.01–3.0 |
| | | | 100.00 |

Ethyl Nicotinate is commercially available from Sigma Chemical Company, Inc. of Saint Louis, MO; ESSENTIAL OIL BLEND #EE-50098 is commercially available from Ungerer Industries Inc. of Bethlehem, PA; SAW PALMETTO EXTRACT is commercially available from Chart Corp., Inc. of Paterson, NJ; NAYAD S and RESPIROGEN are commercially available from Immudyne Inc. of Houston, TX.

Deionized water is metered into a processing tank and high speed mixing is started. In a separate tank the Part B ingredients are heated to 60° C. until dissolved. The Part B ingredients are added to the Part A ingredients and mixed until uniform. Premixed Part C ingredients are then added and mixed until uniform. The Part D ingredients are added and mixed until completely uniform. The result is a light golden yellow, clear, non-viscous liquid having a pH of 3.60–4.20 at 25° C.

Example 12

Mixed Fruit Capsule

A dermatological agent according to the invention is prepared as set forth below:

| Ingredient | Trade Name/Supplier | Amount |
|---|---|---|
| Apple Extract, Apricot Extract, Cherry Extract, Pomegranate Extract, Prune Extract | Mixed Fruit Extract (60% polyphenols)/Nutritional Science Int'l | 10.0–45.0 mg |
| Microcrystalline Cellulose | Microcrystalline Cellulose/Takeda | 330.0–410.0 mg |
| Magnesium Stearate | Magnesium Stearate/Ashland | 5.0–25.0 mg |
| Hydrated Silica | SYLOID #244/Grace Davison | 10.0–35.0 mg |
| | | 435.0 mg/capsule |

Microcrystalline Cellulose is commercially available from Takeda America Inc. of Princeton, NJ; Syloid #244 is commercially available from WR Grace & Co., Grace Davison of Baltimore, MD.

All of the ingredients are blended for 5 minutes in a suitably sized blender and the resulting mixture encapsulated.

Example 13

POM FRUIT™ Pomegranate Capsule

A dermatological agent according to the invention was prepared as set forth below:

| Ingredient | Trade Name/Supplier | Amount |
|---|---|---|
| Pomegranate Extract | Pomegranate Extract (5.4% Ellagic Acid)/Pure World | 10.0–45.0 mg |
| Microcrystalline Cellulose | Microcrystalline Cellulose/Takeda | 330.0–410.0 mg |
| Magnesium Stearate | Magnesium Stearate/Ashland | 5.0–25.0 mg |
| Hydrated Silica | SYLOID #244/Grace Davison | 10.0–35.0 mg |
| | | 435.0 mg/capsule |

Pomegranate Extract is commercially available from Pure World Botanicals Inc. of South Hackensack, NJ.

All of the ingredients are blended for 5 minutes in a suitably sized blender and the resulting mixture encapsulated.

Example 14

Testing Compositions Prepared According to the Invention

Mixed fruit capsules of Example 12 and Pom Fruit™ pomegranate capsules (containing 15 mg of pomegranate extract) of Example 13 were prepared according to the present invention. The capsules were administered to 32 human subjects to evaluate the increase in sun protection factor (SPF) value of four conventional sunscreen formulations following daily ingestion of the capsules for a period of one week. Either one or two capsules were ingested per day. The four sunscreen formulations were conventional formulations of an SPF-4 lotion, an SPF-4 lotion with antioxidants, an SPF-8 lotion, and an SPF-8 lotion with antioxidants. Subjects were healthy male or female volunteers; between 18 and 60 years of age; dependable and capable of following directions; completed a medical history form; and had read, signed, and understood an Informed Consent Form. All subjects were fair skinned with skin types I–III as determined by the following guidelines:

I Always burns easily, never tans (sensitive).

II Always burns easily, tans minimally (sensitive).

III Burns moderately, tans gradually (normal).

IV Burns minimally, always tans well (normal).

V Rarely burns, tans profusely (insensitive).

VI Never burns, deeply pigmented (insensitive).

Subjects were excluded if they had a history of abnormal response to sunlight or taking medication that might produce an abnormal response to sunlight, used alcohol in excess, exhibited current sunburn, suntan, or uneven skin tone that might be confused with a reaction from the test material or that might interfere with evaluation of test results, were pregnant or lactating females, had a known allergy to any of the components of the test articles (i.e., fruits or fruit-derived vitamin supplements), regularly used UVA sunbeds, or exhibited any visible skin disease that could be considered to affect the purpose or integrity of the study.

The following test procedure was followed:

On day 1, the Minimal Erythemal Dose (MED) was determined for each subject. The MED is defined as the time interval or dosage of UV light irradiation sufficient to produce a minimal, perceptible erythema on designated test sites. Prior to the testing phase, the MED of the unprotected skin of each subject was determined by a progressive sequence of timed UV light exposures, graduated incrementally by 25% over that of the previous exposure. The irradiation procedure was based on the method outlined in the Food and Drug Administration monograph of proposed rules for sunscreen testing published in the Federal Register, Vol. 43, No. 166, Aug. 25, 1978. A 150 W Xenon Arc Solar Simulator (commercially available from Solar Light Company of Philadelphia, Pa.) was used as the source of ultraviolet light. A continuous emission spectrum in the UV-B range (290–320 nm) was produced during the testing procedure.

On day 2, sixteen to twenty-four hours after irradiation, the sites were evaluated for erythema according to the following scoring system:

0=Negative, no visible reaction 0.5=Minimal erythema 1.0=Defined erythema 2.0=Moderate erythema 3.0=Severe erythema After grading of the MED, four (4) 5×10 cm test areas were outlined with a surgical marking pen on the subject's back between the scapulae and the beltline, lateral to the midline. These areas were designated as areas 1–4, with an additional area designated for a concurrent MED determination (unprotected control). A 2 mg/cm$^2$ portion of each sunscreen formulation was applied to the appropriate designated test site and spread evenly over the site using a fingercot. The sunscreen formulation that was applied to each site on each subject was determined according to a randomization table. Irradiation of the sites was begun no less than 15 minutes and no longer than 30 minutes after application. The test areas were subdivided into sites, which were used for defined serial UV light exposures. Exposure times were selected for each site in treated areas based upon the previously determined MED of unprotected skin and the expected SPF of the sunscreen formulation.

On day 3, all test sites were evaluated approximately 16 to 24 hours after irradiation to determine minimal erythemal response. After evaluation of the test sites, each subject was instructed to ingest their assigned capsule.

On days 4–9, subjects returned to the clinic to ingest their assigned capsule. All dosing of the capsules was performed under supervision at the clinic.

On day 10, four (4) 5×10 cm test areas were outlined with a surgical marking pen on the subject's back between the scapulae and the beitline, lateral to the midline. These areas were designated as areas 1–4, with an additional area designated for a concurrent MED determination (unprotected control). The application and irradiation procedure performed on Day 2 was repeated as described above.

On day 11, all test sites were evaluated approximately 16 to 24 hours after irradiation to determine minimal erythemal response.

No adverse dermal effects were observed on the treated area of any subject. The pre- and post-ingestion SPF values were then determined for each sunscreen formulation. The SPF is defined as the ratio of the amount of energy or time required to produce an MED on protected skin (treated with sunscreen formulation) to the amount of energy or time needed to produce an MED on untreated skin. The SPF is calculated as follows:

SPF=MED Sunscreen Formulation/MED Unprotected Control

Results are based on eight (8) subjects per test condition, total of thirty-two (32) subjects. Pre- and post-ingestion mean SPF values for each sunscreen formulation and the percent change between the pre-ingestion mean SPF values and the post-ingestion mean SPF values were determined. The t-Test (Dependent) was used to determine if the pre-ingestion mean SPF values of the sunscreen formulations were significantly different than the post-ingestion mean SPF values of the sunscreen formulations. Significance was observed if $P \leq 0.050$. The pre- and post-ingestion mean SPF values for each sunscreen formulation and the percent change from pre-ingestion mean SPF values are reported in Tables I–IV.

TABLE I

Pre- and Post-Ingestion Mean SPF Values for Each Sunscreen Formulation and the Percent Change From Pre-ingestion Mean SPF Values After Administration of One Mixed Fruit Capsule per Day for Seven Days

| Test material | Pre-SPF | Post-SPF | Percent Change | Significance[a] |
|---|---|---|---|---|
| SPF-4 Lotion | 4.91 | 5.01 | 2.0% | n.s. |
| SPF-4 Lotion with Antioxidant | <5.10 | 5.40 | 5.9% | n.s. |
| SPF-8 Lotion | <6.93 | 7.99 | 15.3% | n.s. |
| SPF-8 Lotion with Antioxidant | <8.50 | <8.45 | −0.6% | n.s. |

[a]n.s. = not significant.

TABLE II

Pre- and Post-Ingestion Mean SPF Values
for Each Sunscreen Formulation and the
Percent Change From Pre-ingestion Mean
SPF Values After Administration of Two
Mixed Fruit Capsules per Day for Seven Days

| Test material | Pre-SPF | Post-SPF | Percent Change | Significance[a] |
|---|---|---|---|---|
| SPF-4 Lotion | 4.68 | 5.90 | 26.1% | P < 0.050 |
| SPF-4 Lotion with Antioxidant | 4.93 | 5.86 | 18.9% | P < 0.028 |
| SPF-8 Lotion | <7.26 | 8.45 | 16.4% | n.s. |
| SPF-8 Lotion with Antioxidant | <8.45 | <8.73 | 3.3% | n.s. |

[a]n.s. = not significant.

TABLE III

Pre- and Post-Ingestion Mean SPF Values
for Each Sunscreen Formulation and the
Percent Change From Pre-ingestion Mean
SPF Values After Administration of One
Pomegranate Capsule per Day for Seven Days

| Test material | Pre-SPF | Post-SPF | Percent Change | Significance[a] |
|---|---|---|---|---|
| SPF-4 Lotion | <4.51 | >5.81 | 28.8% | P < 0.078[b] |
| SPF-4 Lotion with Antioxidant | <4.99 | 5.71 | 14.4% | P < 0.014 |
| SPF-8 Lotion | <6.88 | <8.44 | 22.7% | P < 0.027 |
| SPF-8 Lotion with Antioxidant | <8.34 | 10.03 | 20.3% | n.s. |

[a]n.s. = not significant.
[b]Considered near significant at the 92.2% confidence limit.

TABLE IV

Pre- and Post-Ingestion Mean SPF Values
for Each Sunscreen Formulation and the
Percent Change From Pre-ingestion Mean
SPF Values After Administration of Two
Pomegranate Capsules per Day for Seven Days

| Test material | Pre-SPF | Post-SPF | Percent Change | Significance[a] |
|---|---|---|---|---|
| SPF-4 Lotion | 5.08 | 5.60 | 10.2% | n.s |
| SPF-4 Lotion with Antioxidant | 5.10 | >5.68 | 11.4% | n.s |
| SPF-8 Lotion | <6.88 | <7.56 | 9.9% | n.s. |
| SPF-8 Lotion with Antioxidant | 8.55 | >8.91 | 4.2% | n.s. |

[a]n.s. = not significant.

The results of the study show that the post SPF values for SPF-4 lotion and SPF-4 lotion with antioxidants were significantly increased compared to pre-treatment SPF values after ingesting the mixed fruit capsule for one week at a dose of two capsules per day. The results also show that the post SPF values for SPF-4 lotion with antioxidants and the SPF-8 lotion were significantly increased compared to pre-treatment SPF values after ingesting the pomegranate capsule for one week at a dose of one capsule per day. Also, the post SPF values for SPF-4 lotion were significantly increased at the 92.2% confidence limit compared to pre-treatment SPF values after ingesting the pomegranate capsule for one week at a dose of one capsule per day. The results also show that the post SPF values for SPF-4 lotion, SPF-4 lotion with antioxidants, SPF-8 lotion, and SPF-8 lotion with antioxidants were increased compared to pre-treatment SPF values after ingesting the pomegranate capsule for one week at a dose of two capsule per day, these increases, however, were not statistically significant.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. A method for managing one or more dermatological conditions in a patient having skin which comprises topically administering to the patient a therapeutically effective amount of a dermatological agent comprising (a) at least one fruit extract from pomegranate in an amount sufficient to neutralize free radicals; (b) a hydrophilic moisturizing agent in an amount of about 0.01 to 2 weight percent; (c) a hydrophobic moisturizing agent in an amount of about 0.01 to 2 weight percent; (d) a mono- or poly-hydroxy acid in an amount of about 0.01 to 12 weight percent; (e) and a pharmaceutically acceptable carrier.

2. The method of claim 1, wherein the dermatological agent is administered in an amount of between about 1 mg to 20,000 mg per day.

3. The method of claim 1, further comprising administering at least one additional dermatological agent.

4. The method of claim 1, wherein the mono- or poly-hydroxy acid is selected from the group consisting of glycolic acid, lactic acid, citric acid, tannic acid, salicylic acid, and mixtures thereof.

5. The method of claim 1, wherein the hydrophobic agent is selected from the group consisting of ceramide, borage oil, tocopherol linoleate, dimethicone, glycerine, and mixtures thereof.

6. The method of claim 1, wherein the hydrophilic agent is selected from the group consisting hyaluronic acid, sodium peroxylinecarbolic acid, wheat protein, hair keratin amino acids, and mixtures thereof.

7. The method of claim 1, which further comprises orally administering a moisturizing agent selected from the group consisting of primrose oil, GLA 3, flax seed oil, and mixtures thereof.

8. The method of claim 3, wherein the at least one additional dermatological agent comprises a sunscreen or sunblock component.

9. The method of claim 8, wherein the sunscreen or sunblock component is selected from the group consisting of titanium dioxide, zinc oxide, talc, red veterinary petrolatum, a cinnamate, a benzone, a salicylate, a benzoic acid, a benzophenone, and mixtures thereof.

10. The method of claim 3, wherein the at least one additional dermatological agent comprises a component selected from a cysteine component, a magnesium component, a manganese component, or a selenium component.

11. The method of claim 3, wherein the at least one additional dermatological agent comprising at least one of wild yam root, yellow dock, bupleurum, poria cocos, gentian root, myrrh gum, hawthorn berry extract, marshmallow root, rosemary extract, black cohosh, soy, or ginger.

12. The method of claim 3, wherein the at least one additional dermatological agent is an anti-inflammatory component provided in an amount sufficient to inhibit or reduce inflammation.

13. The method of claim 12, wherein the at least one additional anti-inflammatory component is selected from the group consisting of a vitamin E source, a transition metal component, aloe vera gel, aloe vera, licorice extract, pilewort, Canadian willow root, zinc, arnica, allantoin, and mixtures thereof.

14. The method of claim 3, wherein the at least one additional dermatological agent is an immunity boosting component in an amount sufficient to stimulate the patient's immune system response to facilitate repair of damaged skin.

15. The method of claim 14, wherein the immunity boosting component is selected from the group consisting of echinacea extract, golden seal, and mixtures thereof.

16. The method of claim 3, wherein the at least one additional dermatological agent is an antioxidant selected from the group consisting of a catechin-based preparation, a vitamin A source, a ginko biloba extract, a silymarin source, a quercetin compound, a vitamin C source, a carotenoid, and mixtures thereof.

17. The method of claim 3, wherein the at least one additional dermatological agent is administered concurrently with the dermatological agent.

18. A method for managing one or more dermatological conditions in a patient which comprises topically administering to the patient a therapeutically effective amount of a dermatological supplement comprising at least one fruit extract in an amount sufficient to neutralize free radicals; a transition metal component in an amount sufficient to inhibit or reduce inflammation; a hydrophilic moisturizing agent in an amount of about 0.01 to 2 weight percent; a hydrophobic moisturizing agent in an amount of about 0.01 to 2 weight percent; a mono- or poly-hydroxy acid in an amount of about 0.01 to 12 weight percent; and a pharmaceutically acceptable carrier.

19. The method of claim 18, wherein the at least one fruit extract is selected from the group consisting of apricots, apples, pears, peaches, pineapples, papayas, pomegranates, cherries, kiwis, tangerines, grapes, oranges, and mixtures thereof.

20. The method of claim 18, wherein the transition metal component comprises zinc.

21. The method of claim 18, further comprising administering at least one additional dermatological agent.

22. The method of claim 18, wherein the at least one additional dermatological agent comprises a sunscreen or sunblock.

23. The method of claim 19, wherein the at least one additional dermatological agent is administered concurrently with the dermatological supplement.

24. The method of claim 18, wherein the mono- or poly-hydroxy acid is selected from the group consisting of glycolic acid, lactic acid, citric acid, tannic acid, salicylic acid, and mixtures thereof.

25. The method of claim 18, wherein the hydrophobic agent is selected from the group consisting of ceramide, borage oil, tocopherol linoleate, dimethicone, glycerine, and mixtures thereof.

26. The method of claim 18, wherein the hydrophilic agent is selected from the group consisting of hyaluronic acid, sodium peroxylinecarbolic acid, wheat protein, hair keratin amino acids, and mixtures thereof.

27. The method of claim 18, which further comprises orally administering a moisturizing agent selected from the group consisting of primrose oil, GLA 3, flax seed oil, and mixtures thereof.

* * * * *

UNITED STATES PATENT AND TRADEMARK OFFICE
CERTIFICATE OF CORRECTION

PATENT NO.    : 6,630,163 B1
DATED         : October 7, 2003
INVENTOR(S)   : Howard Murad Page 1 of 1

It is certified that error appears in the above-identified patent and that said Letters Patent is hereby corrected as shown below:

Column 38,
Line 14, replace "18" with -- 21 --.
Line 17, replace "19" with -- 21 --.

Signed and Sealed this

Twenty-second Day of June, 2004

JON W. DUDAS
*Acting Director of the United States Patent and Trademark Office*